US010647770B2

(12) United States Patent
Shibayama et al.

(10) Patent No.: US 10,647,770 B2
(45) Date of Patent: *May 12, 2020

(54) THERAPEUTIC AGENT FOR AUTOIMMUNE DISEASES COMPRISING PD-1 AGONIST

(71) Applicant: ONO PHARMACEUTICAL CO., LTD., Osaka-shi, Osaka (JP)

(72) Inventors: Shiro Shibayama, Tsukuba (JP); Masamichi Imai, Tsukuba (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 341 days.

This patent is subject to a terminal disclaimer.

(21) Appl. No.: 15/619,269

(22) Filed: Jun. 9, 2017

(65) Prior Publication Data

US 2017/0320949 A1    Nov. 9, 2017

Related U.S. Application Data

(63) Continuation of application No. 14/237,947, filed as application No. PCT/JP2012/070498 on Aug. 10, 2012, now Pat. No. 9,701,749.

(30) Foreign Application Priority Data

Aug. 11, 2011 (JP) ................................. 2011-176022

(51) Int. Cl.
  *C07K 16/28* (2006.01)
  *A61K 39/395* (2006.01)
  *A61K 45/06* (2006.01)
  *A61K 39/00* (2006.01)

(52) U.S. Cl.
  CPC ........ *C07K 16/2809* (2013.01); *A61K 39/395* (2013.01); *A61K 45/06* (2013.01); *C07K 16/2818* (2013.01); *A61K 2039/505* (2013.01); *A61K 2300/00* (2013.01); *C07K 2317/31* (2013.01); *C07K 2317/75* (2013.01)

(58) Field of Classification Search
None
See application file for complete search history.

(56) References Cited

U.S. PATENT DOCUMENTS

| 7,563,869 | B2 | 7/2009 | Honjo | |
|---|---|---|---|---|
| 7,883,703 | B2 * | 2/2011 | Weiner | C07K 16/2809 424/144.1 |
| 7,998,479 | B2 * | 8/2011 | Honjo | C07K 16/2803 424/130.1 |
| 8,246,955 | B2 * | 8/2012 | Honjo | C07K 16/2803 424/136.1 |
| 8,481,022 | B2 * | 7/2013 | Lodie | A61K 35/28 424/144.1 |
| 8,951,518 | B2 * | 2/2015 | Honjo | C07K 16/2803 424/136.1 |
| 9,701,749 | B2 * | 7/2017 | Shibayama | A61K 39/395 |
| 9,783,609 | B2 * | 10/2017 | Honjo | C07K 16/2803 |
| 2002/0160000 | A1 | 10/2002 | Wood et al. | |
| 2004/0241745 | A1 | 12/2004 | Honjo et al. | |
| 2006/0210567 | A1 * | 9/2006 | Collins | C07K 16/2803 424/146.1 |
| 2007/0092504 | A1 | 4/2007 | Carreno | |
| 2007/0202100 | A1 | 8/2007 | Wood et al. | |
| 2008/0025979 | A1 * | 1/2008 | Honjo | C07K 16/2803 424/136.1 |
| 2009/0076250 | A1 | 3/2009 | Honjo et al. | |
| 2009/0217401 | A1 | 8/2009 | Korman et al. | |
| 2009/0263865 | A1 | 10/2009 | Honjo et al. | |
| 2009/0324609 | A1 | 12/2009 | Lodie et al. | |
| 2011/0171215 | A1 * | 7/2011 | Davis | C07K 16/2818 424/133.1 |
| 2011/0229461 | A1 | 9/2011 | Tyson | |
| 2011/0280878 | A1 | 11/2011 | Honjo et al. | |
| 2013/0022629 | A1 * | 1/2013 | Sharpe | C07D 213/76 424/184.1 |
| 2013/0164294 | A1 | 6/2013 | Honjo et al. | |

FOREIGN PATENT DOCUMENTS

| JP | 2010-229134 A | 10/2010 |
|---|---|---|
| WO | 01/14557 A1 | 3/2001 |
| WO | 02/078731 A1 | 10/2002 |
| WO | 03/011911 A1 | 2/2003 |
| WO | 2004/072286 A1 | 8/2004 |

OTHER PUBLICATIONS

Rose N.R. Am J Epidemiol. 2016; 183 (5): 403-406.*
ATCC entry for hybridoma CRL-8001, 2 pages, accessed on Dec. 7, 2019 at https://www.atcc.org/Products/All/CRL-8001.aspx#characteristics.*
Japanese Patent Office ; Communication dated Oct. 6, 2017 in counterpart application No. 2017-024163.
Abiru, Norio, "Antigen specific treatment for the inhibition and remission of type 1 diabetes," The Japan Society for Clinical Immunology; vol. 31, No. 6; Dec. 2008; pp. 432-439.
Communication dated Oct. 27, 2016, issued by the European Patent Office in counterpart European Application No. 12821886.4.
Communication issued Mar. 18, 2016, issued by the European Patent Office in counterpart European Patent Application No. 12821886.4.
Extended European Search Report dated Mar. 11, 2015 issued by the European Patent Office in counterpart European Patent Application No. 12821886.4.

(Continued)

*Primary Examiner* — Ilia I Ouspenski
(74) *Attorney, Agent, or Firm* — Sughrue Mion, PLLC

(57) ABSTRACT

Provided is a prophylactic, symptom progress-suppressive, and/or therapeutic agent for an autoimmune disease. The agent lowers the risk of infections and reduces the burden of administration to patients. The prophylactic, symptom progress-suppressive, and/or therapeutic agent includes a PD-1 agonist as an active ingredient and is administered (a) 1 to 10 times within one month from the first administration, (b) in a total PD-1 agonist dose of 20 to 1250 μg/kg, and (c) without requiring administration for at least 3 months after the last administration.

21 Claims, 11 Drawing Sheets

Specification includes a Sequence Listing.

(56) References Cited

OTHER PUBLICATIONS

International Search Report, dated Nov. 6, 2012, issued by the International Searching Authority in counterpart International Application No. PCT/JP2012/070498.
Kasagi et al., "Anit-Programmed Cell Death 1 Antibody Reduces CD4+PD-1+T Cells and Relieves the Lupus-like Nephritis of NZB/W F1 Mice", The Journal of Immunology, Mar. 1 2010, pp. 2337-2347, 12 pages total, vol. 184 No. 5, The American Association of Immunologist, Inc., Bethesda, Maryland, USA.
"PD-1 Antibody (J43)", Retrieved from the Internet: URL:https://www.novusbio.com/products/pd-1-antibody-j43_nbp1-43110, 2016, total 7 pages.
Notification of Reasons for Refusal dated Oct. 27, 2016, issued by the Japanese Intellctual Property Office in counterpart Japanese Application No. 2013-528081.
W Chen, et al., "Attenuation of the programmed cell death-1 pathway increases the M1 polarization of macrophages induced by zymosan", Cell Death & Disease 2016, vol. 7, 2016, p. e2115, total 10 pages.
Communication dated May 18, 2016, issued by the Japanese Patent Office in counterpart Japanese Patent Application No. 2013-528081.
Okazaki, Taku et al., "PD-1 and PD-1 ligands: from discovery to clinical application," International Immunology, vol. 19, No. 7, 2007, pp. 813-824.
Keymeulen, Bart et al., "Insulin Needs after CD3-Antibody Therapy in New-Onset Type 1 Diabetes," The New England Journal of Medicine; vol. 352, No. 25; Jun. 23, 2005; pp. 2598-2608.
Kasagi, Shimpei et al., "Anti-PD-1 antibody reduces CD4+PD-1+T cells and relieves the lupus-like nephritis of NZB/W F1 mice," Proceedings of the Japanese Society for Immunology; vol. 39; Nov. 10, 2009; p. 160 (2 pages total).
European Patent Office; Communication dated Nov. 21, 2018 in counterpart application No. 12821886.4.
Thibult et al., "PD-1 is a novel regulator of human B-cell activation", International Immunology, Feb. 2013, vol. 25, No. 2, pp. 129-137 (9 pages total).
Office Action dated Aug. 18, 2017 by the European Patent Office in counterpart European Patent Application No. 12821886.4.

* cited by examiner

SEQUENCE LISTING

```
<160> NUMBER OF SEQ ID NOS: 18

<210> SEQ ID NO 1
<211> LENGTH: 119
<212> TYPE: PRT
<213> ORGANISM: Mus musculus

<400> SEQUENCE: 1

Gln Val Gln Leu Gln Glu Ser Gly Pro Gly Leu Val Lys Pro Ser Gln
1               5                   10                  15

Ser Leu Ser Leu Thr Cys Thr Val Thr Gly His Ser Ile Thr Ser Asp
            20                  25                  30

Tyr Ala Trp Asn Trp Ile Arg Gln Phe Pro Gly Asp Lys Leu Glu Trp
        35                  40                  45

Met Gly Tyr Ile Ser Tyr Ser Gly Tyr Thr Thr Tyr Asn Pro Ser Leu
    50                  55                  60

Lys Ser Arg Val Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Phe Cys
                85                  90                  95

Ala Arg Asp Leu Asp Tyr Gly Pro Trp Phe Ala Tyr Trp Gly Gln Gly
            100                 105                 110

Thr Thr Val Thr Val Ser Ser
        115
```

<210> SEQ ID NO 2
<211> LENGTH: 108
<212> TYPE: PRT
<213> ORGANISM: Mus musculus

<400> SEQUENCE: 2

Asp Ile Gln Met Thr Gln Ser Pro Ala Ser Leu Ser Ala Ser Val Gly
1               5                   10                  15

Glu Thr Val Thr Leu Thr Cys Arg Ala Ser Glu Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Val Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ser Pro Trp
                85                  90                  95

Thr Phe Gly Gly Gly Thr Lys Leu Glu Ile Lys Arg
            100                 105

<210> SEQ ID NO 3
<211> LENGTH: 113
<212> TYPE: PRT
<213> ORGANISM: Homo sapiens

<400> SEQUENCE: 3

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 4
<211> LENGTH: 107
<212> TYPE: PRT
<213> ORGANISM: Homo sapiens

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Ile Ile
        35                  40                  45

Tyr Asp Ala Ser Asn Arg Ala Thr Gly Ile Pro Ala Arg Phe Ser Gly
    50                  55                  60

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
            100                 105

<210> SEQ ID NO 5
<211> LENGTH: 5
<212> TYPE: PRT
<213> ORGANISM: Homo sapiens

<400> SEQUENCE: 5

Asn Ser Gly Met His
1               5

<210> SEQ ID NO 6
<211> LENGTH: 17
<212> TYPE: PRT
<213> ORGANISM: Homo sapiens

<400> SEQUENCE: 6

Val Ile Trp Tyr Asp Gly Ser Lys Arg Tyr Tyr Ala Asp Ser Val Lys
1               5                   10                  15

Gly

<210> SEQ ID NO 7
<211> LENGTH: 4
<212> TYPE: PRT
<213> ORGANISM: Homo sapiens

<400> SEQUENCE: 7

Asn Asp Asp Tyr
1

<210> SEQ ID NO 8
<211> LENGTH: 11
<212> TYPE: PRT
<213> ORGANISM: Homo sapiens

<400> SEQUENCE: 8

Arg Ala Ser Gln Ser Val Ser Ser Tyr Leu Ala
1               5                   10

<210> SEQ ID NO 9
<211> LENGTH: 7
<212> TYPE: PRT
<213> ORGANISM: Homo sapiens

<400> SEQUENCE: 9

Asp Ala Ser Asn Arg Ala Thr
1               5

<210> SEQ ID NO 10
<211> LENGTH: 9
<212> TYPE: PRT
<213> ORGANISM: Homo sapiens

<400> SEQUENCE: 10

Gln Gln Ser Ser Asn Trp Pro Arg Thr
1               5
```

<210> SEQ ID NO 11
<211> LENGTH: 119
<212> TYPE: PRT
<213> ORGANISM: Mus musculus

<400> SEQUENCE: 11

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 12
<211> LENGTH: 107
<212> TYPE: PRT
<213> ORGANISM: Mus musculus

<400> SEQUENCE: 12

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
            100                 105

<210> SEQ ID NO 13
<211> LENGTH: 5
<212> TYPE: PRT
<213> ORGANISM: Mus musculus

<400> SEQUENCE: 13

Arg Tyr Thr Met His
1               5

<210> SEQ ID NO 14
<211> LENGTH: 17
<212> TYPE: PRT
<213> ORGANISM: Mus musculus

<400> SEQUENCE: 14

```
Tyr Ile Asn Pro Ser Arg Gly Tyr Thr Asn Tyr Asn Gln Lys Phe
1               5                   10                  15

Lys Asp

<210> SEQ ID NO 15
<211> LENGTH: 10
<212> TYPE: PRT
<213> ORGANISM: Mus musculus

<400> SEQUENCE: 15

Tyr Tyr Asp Asp His Tyr Cys Leu Asp Tyr
1               5                   10

<210> SEQ ID NO 16
<211> LENGTH: 10
<212> TYPE: PRT
<213> ORGANISM: Mus musculus

<400> SEQUENCE: 16

Ser Ala Ser Ser Ser Val Ser Tyr Met Asn
1               5                   10

<210> SEQ ID NO 17
<211> LENGTH: 7
<212> TYPE: PRT
<213> ORGANISM: Mus musculus

<400> SEQUENCE: 17

Asp Thr Ser Lys Leu Ala Ser
1               5

<210> SEQ ID NO 18
<211> LENGTH: 9
<212> TYPE: PRT
<213> ORGANISM: Mus musculus

<400> SEQUENCE: 18

Gln Gln Trp Ser Ser Asn Pro Phe Thr
1               5
```

THERAPEUTIC AGENT FOR AUTOIMMUNE DISEASES COMPRISING PD-1 AGONIST

CROSS REFERENCE TO RELATED APPLICATIONS

This is a Continuation of U.S. application Ser. No. 14/237,947 (allowed) filed Apr. 9, 2014, which is a National Stage of International Application No. PCT/JP2012/070498 filed Aug. 10, 2012, claiming priority based on Japanese Patent Application No. 2011-176022 filed Aug. 11, 2011, the contents of all of which are incorporated herein by reference in their entirety.

TECHNICAL FIELD

The present invention relates to an autoimmune disease therapeutic agent comprising a PD-1 agonist as an active ingredient. Specifically, the invention relates to an autoimmune disease therapeutic agent for administering a PD-1 agonist at a specific dose and dose regimen.

BACKGROUND ART

Autoimmune diseases are disorders of abnormally accelerating immune responses to self tissues and are generally treated with steroid administration and further treated with continuous administration of immunosuppressive agents such as cyclosporin and methotrexate. These agents, however, not only suppress the autoimmune response, but also suppress immune responses to pathogen infections. Consequently, the management of administration of such agents imposes a burden on patients and medical personnel.

PD-1 is an immunosuppressive receptor belonging to an immunoglobulin family and is a molecule having a function of suppressing the immune activation signals of T-cells activated by stimulation through an antigen receptor. For example, analysis of PD-1 knock-out mice demonstrates that PD-1 signals play important roles in suppression of autoimmune diseases such as autoimmune dilated cardiomyopathy, lupus-like syndrome, autoimmune encephalomyelitis, systemic lupus erythematosus, graft-versus-host disease, type I diabetes mellitus, and rheumatoid arthritis. Accordingly, an agent enhancing the PD-1 signal, that is, a PD-1 agonist is a prophylactic or therapeutic agent for autoimmune diseases.

PD-1 bispecific antibodies (Patent Literatures 1 to 3) have been recognized as a PD-1 agonist. The bispecific antibodies are composed of an antigen-recognition site of an antibody recognizing CD3 and an antigen-recognition site of an antibody recognizing PD-1 linked to each other using genetic engineering. The CD3 is a member of a T-cell receptor complex. The bispecific antibodies enhance the inhibitory signal of PD-1 against the T-cell receptor complex by increasing the frequency of bringing the PD-1 to the periphery of the T-cell receptor complex. Patent Literatures 1 to 3 also state that PD-1 bispecific antibodies can be used for prophylaxis or therapy of autoimmune diseases.

However, there is no knowledge about prescription of PD-1 agonist, to sustain the therapeutic effects with a small number of times of administration and thereby to reduce the burden of administration to patients while lowering the risk of infections.

CITATION LIST

Patent Literature

Patent Literature 1: International Publication No. WO01/014557

Patent Literature 2: International Publication No. WO03/011911

Patent Literature 3: International Publication No. WO04/072286

SUMMARY OF INVENTION

Technical Problem

It is an object of the present invention to provide a prophylactic, symptom progress-suppressive, or therapeutic agent for an autoimmune disease that lowers the risk of infections and reduces the burden of administration to patients.

Solution to Problem

The present inventors have diligently studied and have focused on a PD-1 agonist as an agent to solve the above-mentioned problems and have further found that the above-mentioned problems are solved by prescribing the PD-1 agonist at a specific dose and dose regimen.

That is, the present invention relates to:

[1] A prophylactic, symptom progress-suppressive, and/or therapeutic agent for an autoimmune disease, the agent comprising a PD-1 agonist as an active ingredient, wherein (a) the agent is administered 1 to 10 times within one month from a first administration, (b) a total dose of the PD-1 agonist is 20 to 1250 µg/kg, and (c) administration of the agent is not necessary for at least 3 months after a last administration;

[2] A prophylactic, symptom progress-suppressive, and/or therapeutic agent for an autoimmune disease, the agent comprising a PD-1 agonist as an active ingredient, wherein (a) the agent is administered 1 to 10 times within one month from a first administration, (b) a total dose of the PD-1 agonist is 20 to 1250 µg/kg, and (c) the agent is not administered for at least 3 months after a last administration;

[3] The prophylactic, symptom progress-suppressive, and/or therapeutic agent according to the preceding [1] or [2], wherein the autoimmune disease is type I diabetes mellitus, systemic lupus erythematosus, psoriasis, rheumatoid arthritis, an inflammatory bowel disease (e.g., ulcerative colitis or Crohn's disease), hyperthyroidism, autoimmune adrenal insufficiency, autoimmune hemolytic anemia, multiple sclerosis, psoriatic arthritis, Sjogren syndrome, polymyositis, dermatomyositis, or scleroderma;

[4] The prophylactic, symptom progress-suppressive, and/or therapeutic agent according to the preceding [1] or [2], wherein the autoimmune disease is type I diabetes mellitus, multiple sclerosis, or an inflammatory bowel disease (e.g., ulcerative colitis or Crohn's disease);

[5] The prophylactic, symptom progress-suppressive, and/or therapeutic agent according to the preceding [4], wherein the autoimmune disease is type I diabetes mellitus;

[6] The symptom progress-suppressive and/or therapeutic agent according to the preceding [5], wherein a patient of the type I diabetes mellitus is at an early stage or has mild symptoms;

[7] The prophylactic agent according to the preceding [5], wherein the agent is administered to a carrier of a predisposing factor to type I diabetes mellitus not yet showing the onset of type I diabetes mellitus;

[8] The symptom progress-suppressive and/or therapeutic agent according to the preceding [6], wherein a patient at an early stage or having mild symptoms of type I diabetes mellitus preserves at least 10% of insulin secretion activity or β cell function relative to a normal subject;

[9] The prophylactic agent according to the preceding [7], wherein the carrier of any predisposing factor to type I diabetes mellitus not yet showing the onset of type I diabetes mellitus is:

(I) a subject regarded as a borderline type in clinical diagnostic criteria of diabetes mellitus, (II) a subject being positive for at least one selected from anti-islet cell antibodies, anti-GAD antibodies, anti-insulin antibodies, and anti-IA-2 antibodies in presymptomatic diagnosis, or (III) a subject having a family history of autoimmune diseases in relatives in the first or second degree;

[10] The symptom progress-suppressive agent according to any one of the preceding [3] to [6] and [8], achieving, for at least 3 months after a last administration, the followings:

(i) an average insulin daily dose does not increase relative to that before a first administration of the PD-1 agonist, (ii) an average insulin dose is maintained to 0.25 IU/kg/day or less, (iii) an amount of $HbA_{1c}$ is less than 7.5%, or (iv) a blood C-peptide level is maintained at not lower than 90% of the level according to the present invention;

[11] The prophylactic, symptom progress-suppressive, and/or therapeutic agent according to any one of the preceding [1] and [3] to [10], wherein administration of the agent is not required for at least 4 months after the last administration;

[12] The prophylactic, symptom progress-suppressive, and/or therapeutic agent according to any one of the preceding [1] and [3] to [10], wherein administration of the agent is not required for at least 5 months after the last administration;

[13] The prophylactic, symptom progress-suppressive, and/or therapeutic agent according to any one of the preceding [1] and [3] to [10], wherein administration of the agent is not required for at least 6 months after the last administration;

[14] The prophylactic, symptom progress-suppressive, and/or therapeutic agent according to any one of the preceding [1] and [3] to [10], wherein administration of the agent is not required for at least 7 months after the last administration;

[15] The prophylactic, symptom progress-suppressive, and/or therapeutic agent according to any one of the preceding [1] and [3] to [10], wherein administration of the agent is not required for at least 8 months after the last administration;

[16] The prophylactic, symptom progress-suppressive, and/or therapeutic agent according to any one of the preceding [1] and [3] to [10], wherein administration of the agent is not required for at least 9 months after the last administration;

[17] The prophylactic, symptom progress-suppressive, and/or therapeutic agent according to any one of the preceding [1] and [3] to [10], wherein administration of the agent is not required for at least 12 months after the last administration;

[18] The prophylactic, symptom progress-suppressive, and/or therapeutic agent according to any one of the preceding [1] and [3] to [10], wherein administration of the agent is not required for at least 15 months after the last administration;

[19] The prophylactic, symptom progress-suppressive, and/or therapeutic agent according to any one of the preceding [1] and [3] to [10], wherein administration of the agent is not required for at least 18 months after the last administration;

[20] The prophylactic, symptom progress-suppressive, and/or therapeutic agent according to any one of the preceding [1] and [3] to [10], wherein administration of the agent is not required for at least 21 months after the last administration;

[21] The prophylactic, symptom progress-suppressive, and/or therapeutic agent according to any one of the preceding [1] and [3] to [10], wherein administration of the agent is not required for at least 24 months after the last administration;

[22] The prophylactic, symptom progress-suppressive, and/or therapeutic agent according to any one of the preceding [1] and [3] to [10], wherein administration of the agent is not required for at least 36 months after the last administration;

[23] The prophylactic, symptom progress-suppressive, and/or therapeutic agent according to any one of the preceding [2] to [9], wherein the agent is not administered for at least 4 months after the last administration;

[24] The prophylactic, symptom progress-suppressive, and/or therapeutic agent according to any one of the preceding [2] to [9], wherein the agent is not administered for at least 5 months after the last administration;

[25] The prophylactic, symptom progress-suppressive, and/or therapeutic agent according to any one of the preceding [2] to [9], wherein the agent is not administered for at least 6 months after the last administration;

[26] The prophylactic, symptom progress-suppressive, and/or therapeutic agent according to any one of the preceding [2] to [9], wherein the agent is not administered for at least 7 months after the last administration;

[27] The prophylactic, symptom progress-suppressive, and/or therapeutic agent according to any one of the preceding [2] to [9], wherein the agent is not administered for at least 8 months after the last administration;

[28] The prophylactic, symptom progress-suppressive, and/or therapeutic agent according to any one of the preceding [2] to [9], wherein the agent is not administered for at least 9 months after the last administration;

[29] The prophylactic, symptom progress-suppressive, and/or therapeutic agent according to any one of the preceding [2] to [9], wherein the agent is not administered for at least 12 months after the last administration;

[30] The prophylactic, symptom progress-suppressive, and/or therapeutic agent according to any one of the preceding [2] to [9], wherein the agent is not administered for at least 15 months after the last administration;

[31] The prophylactic, symptom progress-suppressive, and/or therapeutic agent according to any one of the preceding [2] to [9], wherein the agent is not administered for at least 18 months after the last administration;

[32] The prophylactic, symptom progress-suppressive, and/or therapeutic agent according to any one of the preceding [2] to [9], wherein the agent is not administered for at least 21 months after the last administration;

[33] The prophylactic, symptom progress-suppressive, and/or therapeutic agent according to any one of the preceding [2] to [9], wherein the agent is not administered for at least 24 months after the last administration;

[34] The prophylactic, symptom progress-suppressive, and/or therapeutic agent according to any one of the preceding [2] to [9], wherein the agent is not administered for at least 36 months after the last administration;

[35] The prophylactic, symptom progress-suppressive, and/or therapeutic agent according to any one of the preceding [1] to [34], wherein the agent is administered 1 to 10 times within 19 days from the first administration;

[36] The prophylactic, symptom progress-suppressive, and/or therapeutic agent according to any one of the preceding [1] to [34], wherein the agent is administered 1 to 10 times within 17 days from the first administration;

[37] The prophylactic, symptom progress-suppressive, and/or therapeutic agent according to any one of the preceding [1] to [34], wherein the agent is administered 1 to 10 times within 15 days from the first administration;

[38] The prophylactic, symptom progress-suppressive, and/or therapeutic agent according to any one of the preceding [1] to [34], wherein the agent is administered 1 to 10 times within 13 days from the first administration;

[39] The prophylactic, symptom progress-suppressive, and/or therapeutic agent according to any one of the preceding [1] to [34], wherein the agent is administered 1 to 10 times within 11 days from the first administration;

[40] The prophylactic, symptom progress-suppressive, and/or therapeutic agent according to any one of the preceding [1] to [34], wherein the agent is administered 1 to 10 times within 9 days from the first administration;

[41] The prophylactic, symptom progress-suppressive, and/or therapeutic agent according to any one of the preceding [1] to [34], wherein the agent is administered 1 to 9 times within 8 days from the first administration;

[42] The prophylactic, symptom progress-suppressive, and/or therapeutic agent according to any one of the preceding [1] to [34], wherein the agent is administered 1 to 8 times within 7 days from the first administration;

[43] The prophylactic, symptom progress-suppressive, and/or therapeutic agent according to any one of the preceding [1] to [34], wherein the agent is administered 1 to 7 times within 6 days from the first administration;

[44] The prophylactic, symptom progress-suppressive, and/or therapeutic agent according to any one of the preceding [1] to [34], wherein the agent is administered 1 to 6 times within 5 days from the first administration;

[45] The prophylactic, symptom progress-suppressive, and/or therapeutic agent according to any one of the preceding [1] to [34], wherein the agent is administered 1 to 5 times within 4 days from the first administration;

[46] The prophylactic, symptom progress-suppressive, and/or therapeutic agent according to any one of the preceding [1] to [34], wherein the agent is administered 1 to 4 times within 3 days from the first administration;

[47] The prophylactic, symptom progress-suppressive, and/or therapeutic agent according to any one of the preceding [1] to [34], wherein the agent is administered 1 to 3 times within 2 days from the first administration;

[48] The prophylactic, symptom progress-suppressive, and/or therapeutic agent according to any one of the preceding [1] to [34], wherein the agent is administered once on the first administration day;

[49] The prophylactic, symptom progress-suppressive, and/or therapeutic agent according to any one of the preceding [1] to [48], wherein the total dose of the PD-1 agonist is 30 to 960 µg/kg;

[50] The prophylactic, symptom progress-suppressive, and/or therapeutic agent according to any one of the preceding [1] to [48], wherein the total dose of the PD-1 agonist is 48 to 960 µg/kg;

[51] The prophylactic, symptom progress-suppressive, and/or therapeutic agent according to any one of the preceding [1] to [48], wherein the total dose of the PD-1 agonist is 48 to 480 µg/kg;

[52] The prophylactic, symptom progress-suppressive, and/or therapeutic agent according to any one of the preceding [1] to [48], wherein the total dose of the PD-1 agonist is 48 to 160 µg/kg;

[53] The prophylactic, symptom progress-suppressive, and/or therapeutic agent according to any one of the preceding [1] to [48], wherein the total dose of the PD-1 agonist is 160 to 960 µg/kg;

[54] The prophylactic, symptom progress-suppressive, and/or therapeutic agent according to any one of the preceding [1] to [48], wherein the total dose of the PD-1 agonist is 160 to 480 µg/kg;

[55] The prophylactic, symptom progress-suppressive, and/or therapeutic agent according to any one of the preceding [1] to [48], wherein the total dose of the PD-1 agonist is 480 to 960 µg/kg;

[56] The prophylactic, symptom progress-suppressive, and/or therapeutic agent according to any one of the preceding [1] to [48], wherein the total dose of the PD-1 agonist is 30 to 600 µg/kg;

[57] The prophylactic, symptom progress-suppressive, and/or therapeutic agent according to any one of the preceding [1] to [48], wherein the total dose of the PD-1 agonist is 30 to 300 µg/kg;

[58] The prophylactic, symptom progress-suppressive, and/or therapeutic agent according to any one of the preceding [1] to [48], wherein the total dose of the PD-1 agonist is 30 to 100 µg/kg;

[59] The prophylactic, symptom progress-suppressive, and/or therapeutic agent according to any one of the preceding [1] to [48], wherein the total dose of the PD-1 agonist is 100 to 600 µg/kg;

[60] The prophylactic, symptom progress-suppressive, and/or therapeutic agent according to any one of the preceding [1] to [48], wherein the total dose of the PD-1 agonist is 100 to 300 µg/kg;

[61] The prophylactic, symptom progress-suppressive, and/or therapeutic agent according to any one of the preceding [1] to [48], wherein the total dose of the PD-1 agonist is 100 to 160 µg/kg;

[62] The prophylactic, symptom progress-suppressive, and/or therapeutic agent according to any one of the preceding [1] to [48], wherein the total dose of the PD-1 agonist is 300 to 480 µg/kg;

[63] The prophylactic, symptom progress-suppressive, and/or therapeutic agent according to any one of the preceding [1] to [48], wherein the total dose of the PD-1 agonist is 300 to 600 µg/kg;

[64] The prophylactic, symptom progress-suppressive, and/or therapeutic agent according to any one of the preceding [1] to [48], wherein the total dose of the PD-1 agonist is 300 to 960 µg/kg;

[65] The prophylactic, symptom progress-suppressive, and/or therapeutic agent according to any one of the preceding [1] to [64], wherein the PD-1 agonist is a PD-1 bispecific antibody, a PD-1 agonist antibody, or a PD-1 bispecific protein;

[66] The prophylactic, symptom progress-suppressive, and/or therapeutic agent according to the preceding [65], wherein the PD-1 bispecific antibody is a PD-1-CD3 bispecific antibody;

[67] The prophylactic, symptom progress-suppressive, and/or therapeutic agent according to the preceding [66], wherein the PD-1-CD3 bispecific antibody is a PD-1-CD3 bispecific sc(Fv)$_2$;

[68] The prophylactic, symptom progress-suppressive, and/or therapeutic agent according to any one of the preceding [65] to [67], wherein an antigen binding site of a PD-1 antibody forming the PD-1 bispecific antibody is an antigen binding site of a monoclonal antibody derived from hybridoma clone 17D8, 2D3, 4H1, 5C4, 4A11, 7D3, or 5F4 described in International Publication No. WO2006/121168;

[69] The prophylactic, symptom progress-suppressive, and/or therapeutic agent according to any one of the preceding [65] to [68], wherein an antigen binding site of CD3 antibody forming the PD-1 bispecific antibody is antigen binding site of OKT3, OKT3γ1 (ala-ala), ChAglyCD3 (International Publication No. WO93/19196 (U.S. Pat. No. 5,585,097, issued from the U.S. counterpart application)), or HUM291;

[70] A symptom progress-suppressive and/or therapeutic agent for type I diabetes mellitus, comprising PD-1 agonist as an active ingredient, wherein
(a) the agent is administered to type I diabetes mellitus patient preserving at least 10% of insulin secretion activity or β cell function relative to a normal subject once or 2 to 6 times within 24 hours to 11 days from the first administration;
(b) a total dose of the PD-1 agonist is 30 to 960 μg/kg; and
(c) the agent achieves, for at least 12 months after a last administration, the followings:
(i) an average daily insulin dose does not increase relative to that before the first administration of the PD-1 agonist,
(ii) an average insulin dose is maintained to 0.25 IU/kg/day or less,
(iii) an amount of HbA$_{1c}$ is less than 7.5%, or
(iv) a C-peptide response is maintained at not lower than 90% of the level before the first administration of the PD-1 agonist;

[71] A symptom progress-suppressive and/or therapeutic agent for type I diabetes mellitus, comprising a PD-1 agonist as an active ingredient, wherein
(a) the agent is administered to a type I diabetes mellitus patient preserving at least 10% of an insulin secretion activity or β cell function relative to a normal subject once or 2 to 6 times within 24 hours to 11 days from a first administration;
(b) a total dose of the PD-1 agonist is 30 to 960 μg/kg; and
(c) the agent is not administered for at least 12 months after a last administration;

[72] A symptom progress-suppressive and/or therapeutic agent for type I diabetes mellitus, comprising a PD-1 agonist as an active ingredient, wherein
(a) the agent is administered to a type I diabetes mellitus patient preserving at least 10% of an insulin secretion activity or β cell function relative to a normal subject 4 to 6 times within 3 to 11 days from a first administration;
(b) a total dose of the PD-1 agonist is 300 to 960 μg/kg; and
(c) the agent achieves, for at least 12 months after a last administration, the followings:
(i) an average daily insulin dose does not increase relative to that before the first administration of the PD-1 agonist,
(ii) an average insulin dose is maintained to 0.25 IU/kg/day or less,
(iii) an amount of HbA$_{1c}$ is less than 7.5%, or
(iv) a C-peptide response is maintained at not lower than 90% of the level before the first administration of the PD-1 agonist;

[73] A symptom progress-suppressive and/or therapeutic agent for type I diabetes mellitus, comprising a PD-1 agonist as an active ingredient, wherein
(a) the agent is administered to a type I diabetes mellitus patient preserving at least 10% of an insulin secretion activity or β cell function relative to normal subject 4 to 6 times within 3 to 11 days from a first administration;
(b) a total dose of the PD-1 agonist is 300 to 960 μg/kg; and
(c) the agent is not administered for at least 12 months after a last administration;

[74] A prophylactic agent for type I diabetes mellitus, comprising a PD-1 agonist as an active ingredient, wherein
(a) the agent is administered, 4 to 6 times within 3 to 11 days from a first administration, to:
(I) a subject regarded as a borderline type in clinical diagnostic criteria of diabetes mellitus,
(II) a subject being positive for at least one selected from anti-islet cell antibodies, anti-GAD antibodies, anti-insulin antibodies, and anti-IA-2 antibodies in presymptomatic diagnosis, or
(III) a subject having a family history of autoimmune diseases in relatives in the first or second degree;
(b) a total dose of the PD-1 agonist is 30 to 960 μg/kg; and
(c) the agent prevents the onset of type I diabetes mellitus for at least 12 months after a last administration;

[75] A prophylactic agent for type I diabetes mellitus, comprising a PD-1 agonist as an active ingredient, wherein
p (a) the agent is administered, 4 to 6 times within 3 to 11 days from a first administration, to:
(I) a subject regarded as a borderline type in clinical diagnostic criteria of diabetes mellitus,
(II) a subject being positive for at least one selected from anti-islet cell antibodies, anti-GAD antibodies, anti-insulin antibodies, and anti-IA-2 antibodies in presymptomatic diagnosis, or
(III) a subject having a family history of autoimmune diseases in relatives in the first or second degree;
(b) a total dose of the PD-1 agonist is 300 to 960 μg/kg; and
(c) the agent prevents the onset of type I diabetes mellitus for at least 12 months after a last administration;

[76] The prophylactic, symptom progress-suppressive, and/or therapeutic agent for type I diabetes mellitus according to any one of the preceding [70] to [75], wherein the PD-1 agonist is PD-1-CD3 bispecific sc(Fv)$_2$;

[77] A method for sustaining a symptom progress-suppressive and/or therapeutic effect on an autoimmune disease for at least 3 months after a last administration of a PD-1 agonist, comprising administration of the PD-1 agonist to a patient of the autoimmune disease 1 to 10 times within one month from a first administration in a total dose of 20 to 1250 μg/kg;

[78] A PD-1 agonist for being used for sustaining a symptom progress-suppressive and/or therapeutic effect on an autoimmune disease for at least 3 months after a last administration of the PD-1 agonist, wherein the PD-1 agonist is administered to an autoimmune disease patient 1 to 10 times within one month from a first administration in a total dose of 20 to 1250 μg/kg;

[79] A method for preventing the onset of type I diabetes mellitus for at least 3 months after a last administration of a PD-1 agonist, comprising administration of the PD-1 agonist to a carrier of a predisposing factor to type I diabetes mellitus not yet showing the onset of type I diabetes mellitus 1 to 10 times within one month from a first administration in a total dose of 20 to 1250 µg/kg, wherein the onset of type I diabetes mellitus is prevented for at least 3 months after a last administration; and

[80] A PD-1 agonist for preventing the onset of type I diabetes mellitus for at least 3 months after a last administration of the PD-1 agonist, wherein the PD-1 is administered to a carrier of a predisposing factor to type I diabetes mellitus not yet showing the onset of type I diabetes mellitus 1 to 10 times within one month from a first administration in a total dose of 20 to 1250 µg/kg.

Advantageous Effects of Invention

The prophylactic, symptom progress-suppressive, and/or therapeutic agent for an autoimmune disease of the present invention sustains a prophylactic, symptom progress-suppressive, and/or therapeutic effect on an autoimmune disease for a certain period of time with a small number of times of administration while lowering the risk of infections and reducing the burden of management of the administration for a subject having a risk of developing the autoimmune disease, a patient, or medical personnel.

DESCRIPTION OF EMBODIMENTS

Figure 1:
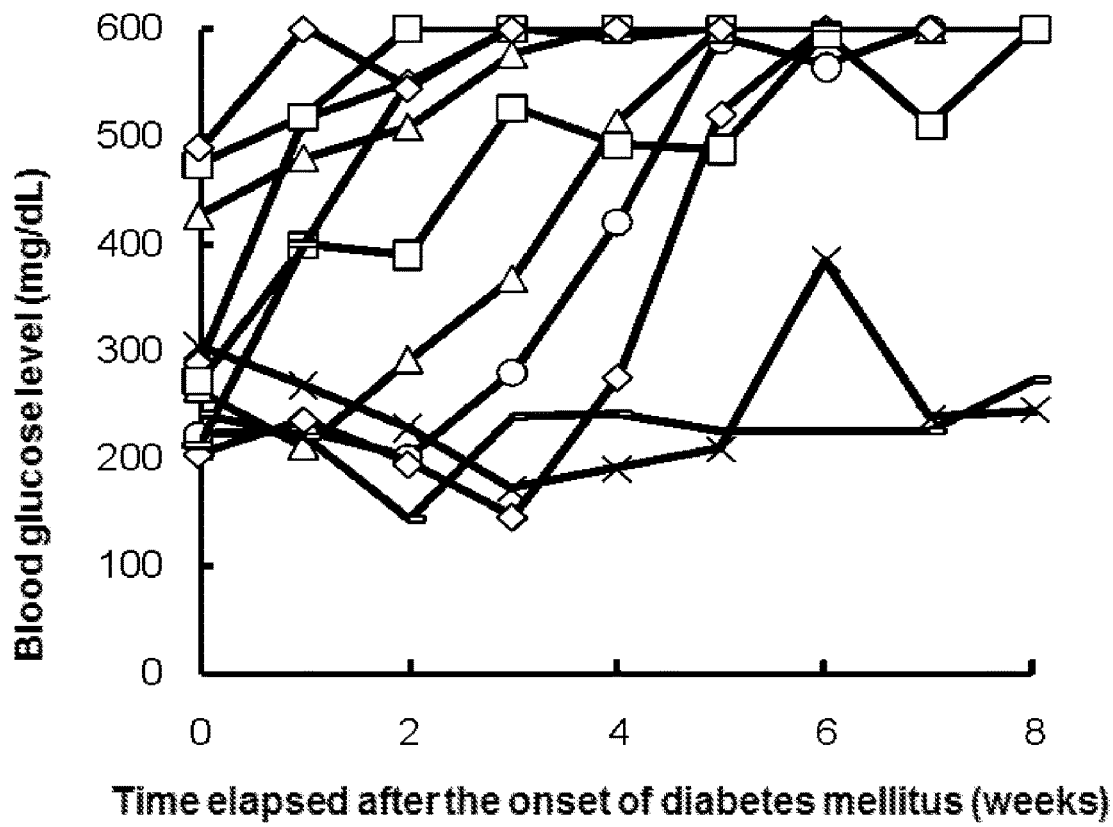
FIG. 1 shows changes in blood glucose level in a control group (phosphate buffer administration group) of a spontaneous type I diabetes mellitus animal model (NOD mice), wherein each line in the graph shows the result of each mouse.

Throughout the specification of the present invention unless specifically defined otherwise, the term "PD-1" refers to human PD-1, and the terms immunostimulatory receptor, a membrane protein forming a complex of the immunostimulatory receptor, and a membrane protein located in the same immunological synapse with the immunostimulatory receptor are refer to those derived from human.

Examples of the immunostimulatory receptor include T-cell receptors (TCRs), B-cell receptors (BCRs), cytokine receptors, LPS receptors, complement receptors, and Fc receptors. Examples of the membrane protein forming an immunostimulatory receptor complex include CD3 and CD79. Examples of the membrane protein located in the same immunological synapse with the immunostimulatory receptors include CD2 and CD19.

In the specification of the present invention, examples of the PD-1 agonist include PD-1 bispecific antibodies, PD-1 agonist antibodies, and PD-1 bispecific proteins.

The term "PD-1 bispecific antibody" refers to an antibody that recognizes both PD-1 and an immunostimulatory receptor, a membrane protein forming a complex of the immunostimulatory receptor, or a membrane protein located in the same immunological synapse with the immunostimulatory receptor. Examples of the PD-1 bispecific antibody include modified antibodies and low-molecular modified antibodies each at least including an antigen binding site of an antibody recognizing PD-1 and an antigen binding site of an antibody recognizing an immunostimulatory receptor, a membrane protein forming a complex of the immunostimulatory receptor, or a membrane protein located in the same immunological synapse with the immunostimulatory receptor. The antigen binding site of an antibody recognizing PD-1 is a site of which the antibody binds to an epitope on the PD-1 and is composed of portions corresponding to the heavy chain variable region (hereinafter, abbreviated to $V_H$) and the light chain variable region (hereinafter, abbreviated to $V_L$) of the anti-PD-1 antibody. The antigen binding site of an antibody recognizing an immunostimulatory receptor, a membrane protein forming a complex of the immunostimulatory receptor, or a membrane protein located in the same immunological synapse with the immunostimulatory receptor is a site of which the antibody binds to an epitope of the immunostimulatory receptor, the membrane protein forming a complex of the immunostimulatory receptor, or the membrane protein located in the same immunological synapse with the immunostimulatory receptor and is composed of portions corresponding to the $V_H$ and the $V_L$ of the antibody.

Examples of the form of the PD-1 bispecific antibody include diabodies, bispecific sc(Fv)$_2$, bispecific minibodies, bispecific F(ab')$_2$, bispecific hybrid antibodies, covalent diabodies (bispecific DART) (International Publication No. WO2006/113665 or WO2008/157379), bispecific (FvCys)$_2$ (J. Immunol. 1992, Vol. 149, No. 1, pp. 120-126), bispecific F(ab'-zipper)$_2$ (J. Immunol. 1992, Vol. 148, No. 5, pp. 1547-1553), bispecific (Fv-zipper)$_2$ (Biochemistry, 1992, Vol. 31, No. 6, pp. 1579-1584), bispecific three-chain antibody (Proc. Natl. Acad. Sci. USA, 1993, Vol. 90, No. 14, pp. 6444-6448), and bispecific mAb$^2$ (www.f-star.com/technology_mab.html).

The diabody is a dimer of single-chain peptides recognizing different antigens and each having a $V_H$ and a $V_L$ linked to each other with a peptide linker (Proc. Natl. Acad. Sci. USA, 1993, Vol. 90, No. 14, pp. 6444-6448). Examples include the dimer which $V_L$a-(L)-$V_H$b and $V_L$b-(L)-$V_H$a are associated by association of $V_H$a with $V_L$a and association of $V_H$b and $V_L$b, wherein $V_H$a and $V_L$a represent each $V_H$ and $V_L$ of an antibody recognizing an antigen "a", $V_H$b and $V_L$b represent each $V_H$ and $V_L$ of an antibody recognizing an antigen "b" and L represents a peptide linker. Each of the $V_H$ and $V_L$ and the peptide linker are linked to one another with peptide bonds. The peptide linker used in the diabody may be any linker that does not hinder the expression of the $V_H$ and $V_L$ to be linked to the respective ends of the linker and does not hinder the formation of the diabody. Examples of the linker include Ser, (Gly)$_n$-Ser, Ser-(Gly)$_n$, ((Gly)$_4$-Ser)$_n$, and (Ser-(Gly)$_4$)$_n$ (n represents an integer of 1 to 6, Ser represents serine, and Gly represents glycine) (J. Immunol. Meth., 1999, Vol. 231, pp. 177-189).

The bispecific sc(Fv)$_2$ is a low-molecular antibody modified such that two pairs of the $V_H$ and $V_L$ of two antibodies recognizing different antigens are linked to each other with a peptide linker into a single chain form (J. Biological Chemistry, 1994, 269: 199-206). Examples of the form of the bispecific sc(Fv)$_2$ can be expressed from the N-terminal side, as follows:

(1) a form of a sequence: $V_H$c-(L$_1$)-$V_H$c-(L$_2$)-$V_H$d-(L$_3$)-$V_L$d, (2) a form of a sequence: $V_L$c-(L$_1$)-$V_H$c-(L$_2$)-$V_H$d-(L$_3$)-$V_L$d, (3) a form of a sequence: $V_H c\text{-}(L_1)\text{-}V_L c\text{-}(L_2)\text{-}V_L d\text{-}(L_3)\text{-}V_H d$, (4) a form of a sequence: $V_H c\text{-}(L_1)\text{-}V_H d\text{-}(L_2)\text{-}V_L d\text{-}(L_3)\text{-}V_L c$, (5) a form of a sequence: $V_L c\text{-}(L_1)\text{-}V_L d\text{-}(L_2)\text{-}V_H d\text{-}(L_3)\text{-}V_H c$, and (6) a form of a sequence: $V_L c\text{-}(L_1)\text{-}V_H d\text{-}(L_2)\text{-}V_L d\text{-}(L_3)\text{-}V_H c$, wherein $V_H c$ and $V_L c$ represent each $V_H$ and $V_L$ of an antibody recognizing an antigen c, $V_H d$ and $V_H d$ represent each $V_H$ and $V_L$ of an antibody recognizing an antigen d, peptide linkers represent $(L_1)$, $(L_2)$, and $(L_3)$, and each of the $V_H$ and $V_L$ and the peptide linker are linked to each other with a peptide bond. The bispecific sc(Fv)$_2$ is formed by association of the $V_H c$ and $V_L c$ and association of the $V_H d$ and $V_L d$. The peptide linkers used may be any linker that does not hinder the expression and the formation of the bispecific sc(Fv)$_2$. Examples of the linker include Ser, $(Gly)_n$-Ser, Ser-$(Gly)_n$, $((Gly)_4$-Ser$)_n$, and (Ser-$(Gly)_4)_n$ (each symbol is synonymous with the above). The three peptide linkers $(L_1)$, $(L_2)$, and $(L_3)$ may be the same as or different from one another.

The bispecific hybrid antibody is an intact antibody composed of two discrete heavy chain/light chain complexes derived from each antibody recognizing each different antigen. The two discrete heavychain/light chain complexes are covalently bound each other, for example, a disulfide bond. The bispecific hybrid antibody can be produced, for example, from a hybridoma using a hybrid hybridoma method (U.S. Pat. No. 4,474,893). Alternatively, the bispecific hybrid antibody can be produced by secretion from a mammal animal cell coexpressing four kinds of cDNAs encoding each heavy chain and each light chain of two kinds of antibodies recognizing a different antigen.

The bispecific F(ab')$_2$ is a low-molecular antibody which each Fab' fragment of antibodies recognizing two different antigens is covalently bonded through, for example, a disulfide bond. The Fab' fragment is an antibody fragment prepared by cleaving the disulfide bond between two heavy chains of F(ab')$_2$ prepared by digestion of an intact antibody with pepsin. The bispecific F(ab')$_2$ can be produced, for example, by maleimidating an Fab' fragment prepared from one antibody with o-phenylenedimaleimide and reacting it with an Fab' fragment prepared from another antibody (Cancer Research, 1997, 57: 4008-4014). Alternatively, a method for chemically binding an Fab' fragment-thionitrobenzoic acid derivative to an antibody fragment of another antibody, such as Fab'-SH, is also known (Science, 1985, 229: 81-83).

The bispecific minibody is a low-molecular antibody which each low-molecular fragment of antibodies modified such that the constant region CH3 domains of the antibodies are linked to scFv recognizing different antigens is covalently bonded with, for example, the disulfide bonds on the CH3 domains (Biochemistry, 1992, Vo. 31, No. 6, pp. 1579-1584). The scFv is a low-molecular modified antibody fragment in a single chain form of a $V_H$ and a $V_L$ linked with, for example, a peptide linker (J. Immunol. Meth., 1999, Vol. 231, pp. 177-189).

In a case an anti-PD-1 antibody and the antibody recognizing an immunostimulatory receptor, a membrane protein forming a complex of the immunostimulatory receptor, and/or a membrane protein located in the same immunological synapse with the immunostimulatory receptor are non-human-derived antibodies, the PD-1 bispecific antibody of the present invention can be produced by humanizing them or converting them into chimera antibodies. Alternatively, the PD-1 bispecific antibody can be produced using each human-type antibody. Throughout the specification, the term "humanized antibody" refers to an antibody prepared by, for example, grafting a complementarity determining region (hereinafter, referred to as CDR) of an antibody derived from a mammal other than human, such as mouse, into the framework (hereinafter, referred to as FR) sequence of a human antibody. For example, the humanized antibody can be produced in accordance with a method described in U.S. Pat. Nos. 4,816,567, 5,225,539, 5,530,101, 5,585,089, or 6,180,370. Alternatively, an amino acid of FR in the variable region of an antibody may be substituted such that the CDR of the humanized antibody forms an appropriate antigen binding site (Cancer Research, Vol. 53, pp. 851-856 (1993)). The chimera antibody is an antibody composed of a variable region sequence derived from a mammal other than human and a constant region sequence derived from human, such as an antibody composed of a variable region sequence derived from a mouse antibody or a rat antibody and a constant region sequence derived from a human antibody. The human-type antibody is an antibody in which the CDR and FR of the variable region and all compositions of the constant region are derived from human and can be produced using HuMAb mouse (trade name) (e.g., see U.S. Pat. Nos. 5,545,806, 5,569,825, 5,625,126, and 5,633,425), KM mouse (trade name) (see International Publication No. WO2002/43478), XenoMouse (trade name) (see U.S. Pat. Nos. 5,939,598, 6,075,181, 6,114,598, 6,150,584, and 6,162,963), TC mouse (trade name) (Proc. Natl. Acad. Sci. USA, Vol. 97, No. 2, pp. 722-727 (2000)), or human immune cell reconstructed SCID mouse (see U.S. Pat. Nos. 5,476,996 and 5,698,767). Alternatively, the human-type antibody can also be prepared by phage display method for screening human immunoglobulin gene libraries (e.g., see U.S. Pat. Nos. 5,565,332, 5,733,743, 5,858,657, 5,223,409, 5,403,484, and 5,571,698).

The series of modified antibodies exemplified as forms of the PD-1 bispecific antibody of the present invention can be produced by modification of genes encoding the respective portions corresponding to the $V_H$ and $V_L$ forming the antigen recognition sites. The genes encoding the portions corresponding to the $V_H$ and $V_L$ can be usually obtained by gene cloning from antibody gene libraries or from hybridomas producing monoclonal antibodies.

The method for obtaining a gene from an antibody gene library, such as antibody phage library (EMBO J., 1993, Vol. 12, No. 2, pp. 725-34, U.S. Pat. No. 5,565,332), is well known and can be performed using a Recombinant Phage Antibody System available from GE Healthcare, Inc. or SurfZAP (trade name) Phage Display Kit available from Stratagene Inc.

Gene cloning for obtaining a gene from a hybridoma producing a monoclonal antibody is also already well known, and cDNAs encoding each portion corresponding to the $V_H$ and $V_L$ of the antibody produced by hybridomas can be cloned by a well-known process from the hybridomas prepared, for example, in accordance with the method of Milstein et al. (Methods Enzymol., 1981, Vol. 73, pp. 3-46).

The PD-1 bispecific antibody of the present invention can be produced by making the antibody express and secrete in a cell transfected by an expression vector inserted an isolated cDNA encoding the $V_H$ and an isolated cDNA encoding the $V_L$. For example, in a case of a diabody, each vector expressing single-chain peptide forming the diabody can be produced using an expression vector having an insertion of a cDNA linked a cDNA encoding the $V_H$ and a cDNA encoding the $V_L$ recognizing each different antigen, respectively, by in-frame to lodge a DNA encoding a peptide linker. The respective DNAs expressing a single-chain peptide may be inserted into a single expression vector or may be inserted into separate expression vectors. A Diabody can be secreted directly by making the expression vectors introduced into appropriate expression cells. In a case, for example, cDNAz encoding two $V_H$ and $V_L$ recognizing their respective antigens are represented as $dV_H a$ and $dV_L a$, $dV_H b$ and $dV_L b$, and DNAs encoding peptide linkers are represented as $dL_1$, $dL_2$, and $dL_3$, a vector expressing a bispecific sc(Fv)$_2$ can be made by, for example, linking in an order such as $dV_H a$-($dL_1$)-$dV_L a$-($dL_2$)-$dV_H b$-($dL_3$)-$dV_L b$ from the 5'-end and inserting it into an expression vector. A bispecific sc(Fv)$_2$ can be secreted directly by making the resulting expression vector introduced into appropriate expression cells. Usable examples of the expression vector for expressing the diabody or bispecific sc(Fv)$_2$ include pCANTAB5E (manufactured by GE Healthcare Biosciences).

Examples of the PD-1 antibody that can be used in production of the PD-1 bispecific antibody of the present invention include the anti-human PD-1 antibody (derived from the hybridoma identified by CNCM deposit No. 1-4122) identified as PD1.3 stated in International Publication No. WO2010/089411, the anti-human PD-1 antibody identified as EH12-1540 stated in International Publication No. WO2010/063011, the anti-human PD-1 antibody identified as EH-12.2H7 stated in International Publication No. WO2010/036959, the anti-human PD-1 antibodies identified as clone 2 (HPA Culture Collection No. 08090903), clone 10 (No. 08090902), and clone 19 (No. 08090901) stated in International Publication No. WO2010/029435, the anti-human PD-1 antibodies identified as 1B8, 28.11, 1.8A10, 1G7, 20B3.1, 7G3, 3H4, 6D10, and 2.3A9 stated in International Publication No. WO2009/114335, the anti-human PD-1 antibodies identified as hPD-1.08A and hPD-1.09A stated in International Publication No. WO2008/156712, the anti-human PD-1 antibodies identified as 10F.9G2 and 10F.2H11 stated in International Publication No. WO2003/042402, the anti-human PD-1 antibody identified as J110 (International Deposit No.: FERM BP-8392) stated in International Publication No. WO2004/072286, and anti-human PD-1 antibodies identified as J105, J108, and J116 stated in Immunology Letters, 2002, Vol. 83, Issue 3, pp. 215-220. Throughout the specification of the present invention, the term "PD-1 antibody" means anti-human PD-1 monoclonal antibody, unless specifically defined otherwise.

The immunostimulatory receptor, a T-cell receptor as the membrane protein forming a complex of the immunostimulatory receptor is composed of an a subunit and a β subunit. The T-cell receptor complex is formed by association of CD3 having subtypes ε, δ, γ and ζ to the T-cell receptor.

When the PD-1 bispecific antibody of the present invention recognizes CD3, the antibody is referred to as PD-1-CD3 bispecific antibody throughout the specification, and the CD3 recognized by the PD-1-CD3 bispecific antibody of the present invention can be an ε, δ, γ, or ζ subtype.

Examples of the CD3 antibody that can be used in production of the PD-1 bispecific antibody of the present invention include OKT3 (ATCC Deposit No. CRL8001) (U.S. Pat. No. 4,658,019), 7D6, 12F6, 38.1, 89b1, 131F26, BL-A8, BW239/347, BW264/56, CD3-4B5, CLB-T3/3, CRIS-7, F111-409, G19-4.1, HIT3a, ICO-90, IP30, Leu-4, LY17.2G3, M-T301, M-T302, MEM-57, MEM-92, NU-T3, OKT3D, SMC2, T3, T3(2Ad2), T3/2Ad2A2, T3/2AD, T3(2ADA), T3/2T8-2F4, T3/RW2-4B6, T3/RW2-8C8, T10B9, T101-01, UCHT1, VIT3, VIT3b, X35-3, XXIII.46, XXIII.87, XXIII.141, YTH12.5, YTH12.5, CLB-T3.4.2, WT31, WT32, SPv-T3b, 11D8, M291, Leu4, 500A2, SP34, RIV-9, BH11, T2/30, AG3, and BC3.

As the CD3 antibody, humanized antibodies such as OKT3γ1 (ala-ala) (U.S. Pat. No. 6,491,916), ChAglyCD3 (International Publication No. WO93/19196 (U.S. Pat. No. 5,585,097, issued from the U.S. counterpart application)), and HUM291 (International Publication No. WO97/44362 (U.S. Pat. No. 5,834,597, issued from the U.S. counterpart application)) are also known. Throughout the specification of the present invention, the term "CD3 antibody" means anti-human CD3 monoclonal antibody, unless specifically defined otherwise.

As the PD-1 antibody, human-type antibodies, such as antibodies identified as 17D8, 2D3, 4H1, 5C4, 4A11, 7D3, and 5F4 stated in International Publication No. WO2006/121168 (U.S. Pat. No. 8,008,449, issued from the U.S. counterpart application) and antibodies identified as PD1-17, PD1-28, PD1-33, and PD1-35 stated in International Publication No. WO2004/056875, are known.

The PD-1 agonist antibodies are intact antibodies, excluding PD-1 bispecific antibodies, having an effect of enhancing the immunosuppressing signal of PD-1. Examples of the antibody include anti-human PD-1 antibodies identified as clone 2 (HPA Culture Collection No. 08090903), clone 10 (No. 08090902), and clone 19 (No. 08090901) stated in International Publication No. WO2010/029435. In the present invention, a plurality of PD-1 agonist antibodies may be used simultaneously or in combination.

The PD-1 bispecific protein is a non-immunoglobulin protein recognizing both PD-1 and an immunostimulatory receptor, a membrane protein forming a complex of the immunostimulatory receptor, or a membrane protein located in the same immunological synapse with the immunostimulatory receptor. Examples of the form of the protein include Adnectin (International Publication No. WO2001/64942), Affibody (trade name) (International Publication Nos. WO95/19374 and WO2000/63243), Anticalin (trade name) (International Publication No. WO99/16873), Avimer (Nature Biotechnology (2005), Vol. 23, pp. 1556-1561), DARPin (Nature Biotechnology (2004), Vol. 22, pp. 575-582), LRRP (Nature (2004), Vol. 430, No. 6996, pp. 174-180), Affitin (Journal of molecular biology (2008), Vol. 383, No. 5, pp. 1058-1068), and Fynomer (International Publication No. WO2011/023685).

Examples of the autoimmune disease that the PD-1 agonist of the present invention can be used as prophylactic, symptom progress-suppressive and/or therapeutic treatment include Behcet disease, systemic lupus erythematosus, multiple sclerosis (systemic scleroderma and progressive systemic scleroderma), scleroderma, polymyositis, dermatomyositis, periarteritis nodosa (polyarteritis nodosa and microscopic polyangiitis), aortitis syndrome (Takayasu arteritis), malignant rheumatoid arthritis, rheumatoid arthritis, Wegner's granulomatosis, mixed connective tissue disease, Sjogren syndrome, adult-onset Still's disease, allergic granulomatous angiitis, hypersensitivity angiitis, Cogan's syndrome, RS3PE, temporal arteritis, polymyalgia rheumatica, fibromyalgia syndrome, antiphospholipid antibody syndrome, eosinophilic fasciitis, IgG4-related diseases (e.g., primary sclerosing cholangitis and autoimmune pancreatitis), Guillain-Barre syndrome, myasthenia gravis, chronic atrophic gastritis, autoimmune hepatitis, primary biliary cirrhosis, aortitis syndrome, Goodpasture's syndrome, rapidly progressive glomerulonephritis, megaloblastic anemia, autoimmune hemolytic anemia, autoimmune neutropenia, idiopathic thrombocytopenic purpura, Graves' disease (hyperthyroidism), Hashimoto's thyroiditis, autoimmune adrenal insufficiency, primary hypothyroidism, idiopathic Addison's disease (chronic adrenal insufficiency), type I diabetes mellitus, chronic discoid lupus erythematosus, localized scleroderma, psoriasis, psoriatic arthritis, pemphigus, pemphigoid, herpes gestationis, linear IgA bullous skin disease, epidermolysis bullosa acquisita, alopecia areata, vitiligo, Harada disease, autoimmune optic neuropathy, idiopathic azoospermia, recurrent fetal loss, and inflammatory bowel diseases (ulcerative colitis and Crohn's disease). The prescription of the present invention can also be applied to prophylaxis or therapy of graft-versus-host disease (GVHD).

Examples of the autoimmune disease patient for whom the prophylactic, symptom progress-suppressive, and/or therapeutic agent comprising the PD-1 agonist of the present invention is effective include a carrier of a predisposing factor to the autoimmune disease not yet showing the onset, a patient at early stages, a patient with a mild symptom, and a patient of recurrence, in addition to a patient diagnosed as having the autoimmune disease and a patient in acute advanced stage.

The carrier of a predisposing factor to an autoimmune disease not yet showing the onset is, for example, as follows:

(I) a subject being positive for a diagnostic marker in presymptomatic testing of an autoimmune disease and having a risk of developing the disease in the future, (II) a subject not satisfying clinical diagnostic criteria but being in borderline, and (III) a subject having a family history of an autoimmune disease in relatives in the first or second degree.

For example, if the autoimmune disease is type I diabetes mellitus, examples of the carrier include:

(I) a subject who are positive, in presymptomatic testing, for at least one selected from, for example, anti-islet cell antibody (anti-ICA512 antibody), anti-glutamate decarboxylase antibody (anti-GAD antibody) such as anti-GAD65 antibody and anti-GAD67 antibody, anti-insulin antibody, and anti-IA-2 antibody;

(II) a subject regarded as a borderline type that is not diagnosed as a diabetic type or a normal type in the clinical diagnostic criteria of diabetes mellitus by the Japan Diabetes Society (2010) enforced on Jul. 1, 2010;

(III) a subject having a family history of an autoimmune disease including type I diabetes mellitus in relatives in the first or second degree;

(IV) a HLA DR7-positive Caucasian, a HLA DR4-positive Black, and a HLA DR9-positive Japanese; and (V) a subject a having history of infection with a early childhood virus (e.g., Coxsackie B virus, enteric virus, adenovirus, rubella, cytomegalovirus, or Epstein-Barr virus).

Herein, in a subject who is positive for at least one selected from anti-islet cell antibody (anti-ICA512 antibody), anti-glutamate decarboxylase antibody (anti-GAD antibody) such as anti-GAD65 antibody and anti-GAD67 antibody, anti-insulin antibody, and anti-IA-2 antibody and the subject having a family history of an autoimmune disease including type I diabetes mellitus in relatives in the first or second degree, a patient who has already been diagnosed with type II diabetes mellitus may be included.

Examples of the patient with an early stage symptom or with a mild symptom of an autoimmune disease, if the autoimmune disease is type I diabetes mellitus, include a patient diagnosed with diabetes mellitus, for the first time, by the clinical diagnostic criteria of diabetes mellitus or already treated with, for example, insulin administration and preserving at least 10% of the $\beta$ cell function relative to a normal subject. The $\beta$ cell function can be evaluated by measuring blood C-peptide level. The blood C-peptide level can be measured by a known method. Examples of the patient with an early stage symptom or with a mild symptom of type I diabetes mellitus also include a patient classified into slowly progressive type I diabetes mellitus (SPIDDM) or latent autoimmune diabetes mellitus in adults (LADA).

In the case of multiple sclerosis, examples of the carrier of predisposing a factor to multiple sclerosis and the patient with an early stage symptom or with a mild symptom of multiple sclerosis include:

(I) a subject having mutation in a gene encoding HLA-DRB1, IL7R-$\alpha$, or IL2R-$\alpha$;

(II) a subject having a history of infection with, for example, Epstein-Barr virus;

(III) a patient who is not diagnosed with multiple sclerosis in McDonald criteria revised in 2005, but diagnosed with "clinically isolated syndrome" or "first clinical symptoms syndrome", which has a risk of transition to multiple sclerosis, defined in differential diagnosis by Miller, et al. (Mult Scler, 2008, Vol. 14, pp. 1157-1174) and a demyelinating disease patient who does not have twice or more clinical symptoms and two or more clinically objective lesions;

(IV) a optic neuromyelitis patient, an anti-aquaporin antibody positive patient, and a patient with a long cord lesion on spinal cord extending over three or more vertebral segments (NMO spectrum disorder) observed by MRI; and (V) a subject recognized with a first clinical symptom in multiple sclerosis diagnostic criteria (2003) by Ministry of Health, Labour and Welfare Immune Neurological Disease Research Group, but not recognized with recurrence.

Examples of the first or recurrent clinical symptom include a clinical symptom of optic neuritis, blurring of vision, diplopia, involuntary rapid eye movement, blindness, loss of the sense of balance, tremors, ataxia, dizziness, uncertain limbs, loss of coordination, weakness of one or more limbs, changes in muscle tonus, muscle stiffness, spasms, tingling, paresthesia, scorching pain, muscle pain, facial pain, trigeminal neuralgia, shooting sharp pain, scorching trigeminal pain, delay of speech, speech difficulty, change in speech rhythm, dysphagia, fatigue, bladder problems (including impendence, frequent urination, incomplete urination, and incontinence), bowel problems (including constipation and loss of bowel control), impotence, reduced sexual desire, loss of the sense, sensitivity to heat, loss of short-term memory, loss of concentration, and loss of judgment or inference.

Examples of the clinically objective lesion include cerebrum, cerebellum, brain stem, spinal cord, optic nerve, and peripheral nerve.

In the present invention, the term "first administration" means the first administration when the agent of the present invention has not been prescribed in the past and also includes the first administration in readministration of the agent of the present invention when the agent was prescribed in the past one or more times and showed a prophylactic, symptom progress-suppressive, or therapeutic effect at least once for a certain period of time, but the readministration of the agent of the present invention is necessary. If the administration of the agent is single administration within one month from the first administration, the single administration is the first administration.

In the present invention, the term "last administration" means the last administration in multiple times of administration in a period of not longer than one month after the most recent first administration. In a case of single administration, the administration is the last administration.

In the present invention, the state that "administration is not required" means that the clinical symptoms of an autoimmune disease are not recognized, the symptom does not progress, or the disease has been cured, even if the PD-1 agonist is not additionally administered or another agent is not administered or not increased in the amount, after administration of the PD-1 agonist at the usage and dose of the present invention.

For example, in the case of type I diabetes mellitus, the state not requiring administration in a carrier of a predisposing factor to type I diabetes mellitus not yet showing the onset means that the carrier is not diagnosed as a diabetic type in the clinical diagnostic criteria of diabetes mellitus by the Japan Diabetes Society (2010). On the other hand, the state not requiring administration in a patient with an early stage symptom or a mild symptom of type I diabetes mellitus is a state that:

(i) an average insulin dose per day is not increased from that before the first administration of the PD-1 agonist, (ii) an average insulin dose can be maintained to 0.25 IU/kg/day or less, (iii) an amount of $HbA_{1c}$ is less than 7.5%, (iv) a blood C-peptide level is not lower than 90% of the level before the first administration of the PD-1 agonist, or (v) cure of type I diabetes mellitus is diagnosed.

The state requiring readministration of the agent of the present invention means, for example, in a case of type I diabetes mellitus, a state that is inferred to be diagnosed as a diabetic type in the clinical diagnostic criteria of diabetes mellitus by the Japan Diabetes Society (2010) after a certain period of time (3 months or more) from the last administration of the agent of the present invention. The state requiring readministration in a patient with an early stage symptom or a mild symptom of type I diabetes mellitus is a state that:

(i) an average insulin dose per day should be increased to be higher than the dose before the first administration of the PD-1 agonist, (ii) an average insulin dose cannot be maintained to 0.25 IU/kg/day or less, (iii) an amount of $HbA_{1c}$ is 7.5% or more, or (iv) a blood C-peptide level is lower than 90% of the level before the first administration of the PD-1 agonist.

In the case of multiple sclerosis, the state requiring readministration of the PD-1 agonist of the present invention to a carrier of a predisposing factor to multiple sclerosis is, for example, (I) a state of a patient who is not diagnosed with multiple sclerosis in McDonald criteria revised in 2005, but diagnosed with "clinically isolated syndrome" or "first clinical symptoms syndrome", which has a risk of transition to multiple sclerosis or (II) a state that first clinical symptoms in multiple sclerosis diagnostic criteria (2003) by Ministry of Health, Labour and Welfare Immune Neurological Disease Research Group are recognized.

Other examples of the state requiring readministration include a state that recurrence or progress of a clinical symptom had been suppressed by administration of the PD-1 agonist of the present invention, but a symptom of recurrence is recognized in a patient diagnosed with multiple sclerosis in the revised McDonald criteria or the multiple sclerosis diagnostic criteria (2003) by Ministry of Health, Labour and Welfare Immune Neurological Disease Research Group, a demyelinating disease patient not diagnosed with multiple sclerosis, a patient diagnosed with clinically isolated syndrome, or a patient diagnosed with optic neuromyelitis or NMO spectrum disorder. The second onset of a clinical symptom or a symptom of recurrence can be examined by, for example, a head MRI image or spinal cord MRI image, cerebrospinal fluid observation such as IgG indices and oligoclonal bands, or a method of detecting a delay in demyelination conduction velocity with evoked brain waves such as measurement of visual evoked potential, measurement of somatosensory evoked potential, measurement of auditory brainstem response, or measurement of magnetic evoked potential.

In the present invention, the term "therapy" means cure or improvement of an autoimmune disease or its symptoms. The term "sustaining of therapeutic effect" means that a state that a symptom is not exacerbated or is improved than before the first administration continues by administration of the PD-1 agonist. The term of "prophylaxis" means that an onset of an autoimmune disease or a symptom is prevented or delayed for a certain period of time. The term "suppression of symptom progress" means that the progress or deterioration of a symptom of an autoimmune disease is suppressed to stop the progress of pathology. The meaning of "prophylaxis" includes prevention of recurrence.

In the present invention, the period of "not requiring administration", in other words, the period from the last administration of the agent of the present invention to the time requiring readministration is at least 3 months, such as at least 4 months, 5 months, 6 months, 7 months, 8 months, 9 months, 12 months, 15 months, 18 months, 21 months, 24 months, or 36 months. During such a period, administration of the agent of the present invention is not required. Herein, the period from the last administration of the PD-1 agonist to the time at which the effect reaches the plateau region (specifically, e.g., 1 to 2 months) is also included in the period of not requiring administration of the PD-1 agonist.

The frequency of administration of the PD-1 agonist of the present invention is 1 to 10 times including the first and the last administration and can be appropriately determined in consideration of the age and weight of a patient, the disease in autoimmune diseases or its symptoms, the dose, route, and period of administration, and the burden to the patient. For example, the frequency of administration can be selected from once, twice, 3 times, 4 times, 5 times, 6 times, 7 times, 8 times, 9 times, and 10 times. The frequency of administration per day is usually once.

The period of administration of the PD-1 agonist of the present invention is within one month from the first administration and can be appropriately determined in consideration of the disease in autoimmune diseases or its symptoms, the burden to a patient, and the dose or frequency of administration. For example, in a case of requiring multiple times of administration, the "period within one month" can be selected from 24 hours, 2 days, 3 days, 4 days, 5 days, 6 days, 7 days, 8 days, 9 days, 11 days, 13 days, 15 days, 17 days, 19 days, and one month, from the first administration. Herein, the day of the last administration is the last day of the administration period.

The intervals of the multiple times of administration within one month from the first administration may be the same as or different from one another.

The "total dose" of the PD-1 agonist of the present invention is the total amount administered 1 to 10 times (i.e., the total administration from the first administration to the last administration) in "the period within one month from the first administration" and can be appropriately determined within a range of 20 to 1250 μg/kg in consideration of the age of a patient, the disease or its symptoms, and the route or time of administration. For example, the total dose can be appropriately selected from the range of 30 to 960 μg/kg, specifically, from (i) a dose of not lower than 30 μg/kg, 48

μg/kg, 60 μg/kg, 96 μg/kg, 100 μg/kg, 120 μg/kg, 160 μg/kg, 180 μg/kg, 192 μg/kg, 240 μg/kg, 288 μg/kg, 300 μg/kg, 384 μg/kg, 480 μg/kg, or 600 μg/kg and not higher than 960 μg/kg, (ii) a dose of not lower than 30 μg/kg, 48 μg/kg, 60 μg/kg, 96 μg/kg, 100 μg/kg, 120 μg/kg, 160 μg/kg, 180 μg/kg, 192 μg/kg, 240 μg/kg, 288 μg/kg, 300 μg/kg, 384 μg/kg, or 480 μg/kg and not higher than 600 μg/kg, (iii) a dose of not lower than 30 μg/kg, 48 μg/kg, 60 μg/kg, 96 μg/kg, 100 μg/kg, 120 μg/kg, 160 μg/kg, 180 μg/kg, 192 μg/kg, 240 μg/kg, 288 μg/kg, 300 μg/kg, or 384 μg/kg and not higher than 480 μg/kg, (iv) a dose of not lower than 30 μg/kg, 48 μg/kg, 60 μg/kg, 96 μg/kg, 100 μg/kg, 120 μg/kg, 160 μg/kg, 180 μg/kg, 192 μg/kg, 240 μg/kg, 288 μg/kg, or 300 μg/kg and not higher than 384 μg/kg, (v) a dose of not lower than 30 μg/kg, 48 μg/kg, 60 μg/kg, 96 μg/kg, 100 μg/kg, 120 μg/kg, 160 μg/kg, 180 μg/kg, 192 μg/kg, 240 μg/kg, or 288 μg/kg and not higher than 300 μg/kg, (vi) a dose of not lower than 30 μg/kg, 48 μg/kg, 60 μg/kg, 96 μg/kg, 100 μg/kg, 120 μg/kg, 160 μg/kg, 180 μg/kg, 192 μg/kg, or 240 μg/kg and not higher than 288 μg/kg, (vii) a dose of not lower than 30 μg/kg, 48 μg/kg, 60 μg/kg, 96 μg/kg, 100 μg/kg, 120 μg/kg, 160 μg/kg, 180 μg/kg, or 192 μg/kg and not higher than 240 μg/kg, (viii) a dose of not lower than 30 μg/kg, 48 μg/kg, 60 μg/kg, 96 μg/kg, 100 μg/kg, 120 μg/kg, 160 μg/kg, or 180 μg/kg and not higher than 192 μg/kg, (ix) a dose of not lower than 30 μg/kg, 48 μg/kg, 60 μg/kg, 96 μg/kg, 100 μg/kg, 120 μg/kg, or 160 μg/kg and not higher than 180 μg/kg, (x) a dose of not lower than 30 μg/kg, 48 μg/kg, 60 μg/kg, 96 μg/kg, 100 μg/kg, or 120 μg/kg and not higher than 160 μg/kg, (xi) a dose of not lower than 30 μg/kg, 48 μg/kg, 60 μg/kg, 96 μg/kg, or 100 μg/kg and not higher than 120 μg/kg, (xii) a dose of not lower than 30 μg/kg, 48 μg/kg, 60 μg/kg, or 96 μg/kg and not higher than 100 μg/kg, (xiii) a dose of not lower than 30 μg/kg, 48 μg/kg, or 60 μg/kg and not higher than 96 μg/kg, (xiv) a dose of not lower than 30 μg/kg or 48 μg/kg and not higher than 60 μg/kg, and (xv) a dose of 30 to 48 μg/kg. More specifically, the dose can be appropriately selected from ranges, for example, 48 to 960 μg/kg, 48 to 480 μg/kg, 48 to 384 μg/kg, 48 to 288 μg/kg, 48 to 192 μg/kg, 48 to 160 μg/kg, 48 to 96 μg/kg, 96 to 960 μg/kg, 96 to 480 μg/kg, 96 to 384 μg/kg, 96 to 288 μg/kg, 96 to 192 μg/kg, 96 to 160 μg/kg, 160 to 960 μg/kg, 160 to 480 μg/kg, 160 to 384 μg/kg, 160 to 288 μg/kg, 160 to 192 μg/kg, 192 to 960 μg/kg, 192 to 480 μg/kg, 192 to 384 μg/kg, 192 to 288 μg/kg, 288 to 960 μg/kg, 288 to 480 μg/kg, 288 to 384 μg/kg, 384 to 960 μg/kg, 384 to 480 μg/kg, 480 to 960 μg/kg, 30 to 600 μg/kg, 30 to 300 μg/kg, 30 to 240 μg/kg, 30 to 180 μg/kg, 30 to 120 μg/kg, 30 to 100 μg/kg, 30 to 60 μg/kg, 100 to 600 μg/kg, 100 to 300 μg/kg, 100 to 240 μg/kg, 100 to 180 μg/kg, 100 to 120 μg/kg, 120 to 600 μg/kg, 120 to 200 μg/kg, 120 to 240 μg/kg, 120 to 180 μg/kg, 180 to 600 μg/kg, 180 to 300 μg/kg, 180 to 240 μg/kg, 240 to 600 μg/kg, 240 to 300 μg/kg, and 300 to 600 μg/kg. The doses in administration at 1 to 10 times may be the same as or different from one another.

In the present invention, the PD-1 agonist is preferably a PD-1 bispecific antibody, more preferably a PD-1-CD3 bispecific antibody, more preferably a bispecific antibody recognizing both PD-1 and CD3ε (hereinafter, may be referred to as PD-1-CD3ε bispecific antibody), and most preferably a bispecific sc(Fv)$_2$ recognizing both PD-1 and CD3ε (hereinafter, may be referred to as PD-1-CD3ε bispecific sc(Fv)$_2$).

The PD-1 antibody that is used for producing the PD-1-CD3 bispecific antibody is preferably a humanized or human-type PD-1 antibody and more preferably a human-type PD-1 antibody. The non-human PD-1 antibody that is used for producing the humanized PD-1 antibody is preferably an anti-human PD-1 antibody identified as J110 (International Deposit No.: FERM BP-8392) or an anti-human PD-1 antibody identified as J105, J108, or J116 stated in Immunology Letters, 2002, Vol. 83, Issue 3, pp. 215-220 and more preferably an anti-human PD-1 antibody identified as J110 (International Deposit No.: FERM BP-8392). The amino acid sequences of the $V_H$ and $V_L$ of J110 are represented by SEQ ID NOs: 1 and 2, respectively.

The human-type PD-1 antibody is preferably a human-type PD-1 antibody identified as 17D8, 2D3, 4H1, 5C4, 4A11, 7D3, or 5F4 stated in International Publication No. WO2006/121168 and more preferably a human-type PD-1 antibody identified as 5C4. The amino acid sequences of the $V_H$ and $V_L$ of 5C4 are represented by SEQ ID NOs: 3 and 4, respectively. The amino acid sequences of CDR1, CDR2, and CDR3 of the $V_H$ are represented by SEQ ID NOs: 5, 6, and 7, respectively. The amino acid sequences of CDR1, CDR2, and CDR3 of the $V_L$ are represented by SEQ ID NOs: 8, 9, and 10, respectively.

The CD3 antibody that is used for producing the PD-1-CD3 bispecific antibody is preferably a humanized or human-type CD3 antibody. The humanized CD3 antibody is preferably a humanized antibody of OKT3 and more preferably OKT3γ1 (ala-ala), ChAglyCD3, or HUM291. The amino acid sequences of the $V_H$ and $V_L$ of OKT3 are represented by SEQ ID NOs: 11 and 12, respectively. The amino acid sequences of CDR1, CDR2, and CDR3 of the $V_H$ are represented by SEQ ID NOs: 13, 14, and 15, respectively. The amino acid sequences of CDR1, CDR2, and CDR3 of the $V_L$ are represented by SEQ ID NOs: 16, 17, and 18, respectively.

Examples of the autoimmune disease to which the agent of the present invention shows a high prophylactic, symptom progress-suppressive, and/or therapeutic effect include type I diabetes mellitus, multiple sclerosis, systemic lupus erythematosus, psoriasis, rheumatoid arthritis, inflammatory bowel diseases (e.g., ulcerative colitis, Crohn's disease), hyperthyroidism, autoimmune adrenal insufficiency, autoimmune hemolytic anemia, psoriatic arthritis, Sjogren syndrome, polymyositis, dermatomyositis, and scleroderma. In particular, the agent is highly effective on type I diabetes mellitus, multiple sclerosis, and inflammatory bowel disease.

The agent of the present invention is preferably administered 1 to 6 times, more preferably 4 to 6 times, and most preferably 5 times. The administration period for the optimum times of administration is preferably 24 hours to 11 days from the first administration, more preferably 3 days, 4 days, 5 days, 7 days, 9 days, or 11 days after the first administration, and most preferably 4 days or 9 days from the first administration.

The dose of the PD-1 agonist in the agent of the present invention is preferably 300 to 960 μg/kg, more preferably 300 to 600 μg/kg, and most preferably 480 to 600 μg/kg.

The PD-1 agonist of the present invention is formulated to be used as an injection or infusion solution for drip infusion. The injection or infusion solution may be in a form of an aqueous solution, suspension, or emulsion or may be formulated as a solid agent such that the agent is dissolved, suspended, or emulsified in a solvent at the time of use. Examples of the solvent that is used in the injection or the infusion solution for drip infusion include distilled water for injection, physiological saline, glucose solutions, and isotonic solutions (e.g., solutions of sodium chloride, potassium chloride, glycerin, mannitol, sorbitol, boric acid, borax, or propylene glycol).

Herein, examples of pharmaceutically acceptable carriers include stabilizers, solubilizers, suspending agents, emulsifiers, soothing agents, buffering agents, preservatives, antiseptic agents, pH adjusters, and antioxidants. Usable examples of the stabilizers include various amino acids, albumin, globulin, gelatin, mannitol, glucose, dextran, ethylene glycol, propylene glycol, polyethylene glycol, ascorbic acid, sodium bisulfite, sodium thiosulfate, sodium edetate, sodium citrate, and dibutylhydroxytoluene. Usable examples of the solubilizers include alcohols (e.g., ethanol), polyols (e.g., propylene glycol and polyethylene glycol), and nonionic surfactants (e.g., Polysorbate 80 (trade name) and HCO-50). Usable examples of the suspending agents include glyceryl monostearate, aluminum monostearate, methyl cellulose, carboxymethyl cellulose, hydroxymethyl cellulose, and sodium lauryl sulfate. Usable examples of the emulsifiers include gum arabic, sodium alginate, and tragacanth. Usable examples of the soothing agents include benzyl alcohol, chlorobutanol, and sorbitol. Usable examples of the buffering agents include phosphate buffer, acetate buffer, borate buffer, carbonate buffer, citrate buffer, Tris buffer, glutamic acid buffer, and epsilon aminocaproic acid buffer. Usable examples of the preservatives include methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, sodium edeate, boric acid, and borax. Usable examples of the antiseptic agents include benzalkonium chloride, parahydroxybenzoic acid, and chlorobutanol. Usable examples of the pH adjusters include hydrochloric acid, sodium hydroxide, phosphoric acid, and acetic acid. Usable examples of the antioxidants includes (1) aqueous antioxidants such as ascorbic acid, cysteine hydrochloride, sodium bisulfate, sodium metabisulfite, and sodium sulfite, (2) oil-soluble antioxidants such as ascorbyl palmitate, butylated hydroxy anisole, butylated hydroxy toluene, lecithin, propyl gallate, and α-tocopherol, and (3) metal chelating agents such as citric acid, ethylenediaminetetraacetic acid, sorbitol, tartaric acid, and phosphoric acid.

The injection or the infusion solution for drip infusion can be produced by performing sterilization or aseptic manipulation, for example, sterilization by filtration with a filter in the final process and subsequently filling an aseptic container with the solution. The injection or the infusion solution for drip infusion may be used by dissolving the vacuum dried or lyophilized aseptic powder (which may include a pharmaceutically acceptable carrier powder) in an appropriate solvent at the time of use.

Furthermore, the PD-1 agonist as an active ingredient of the agent of the present invention may be used in combination with other agent that is used for prophylaxis and/or therapy of an autoimmune disease. In such combination use, the PD-1 agonist can complement the prophylactic and/or therapeutic effect of the other agent or can maintain or reduce the dose or frequency of administration of the other agent. In the present invention, in a case of separately administering the PD-1 agonist and the other agent, the both agents may be simultaneously administered for a certain period of time, and then the other agent only may be administered. Alternatively, the PD-1 agonist of the agent of the present invention may be previously administered, and, after the completion of the administration, the other agent may be administered. Conversely, the other agent may be previously administered, and then the PD-1 agonist of the agent of the present invention may be administered. The routes of administration may be the same as or different from each other. The present invention also can provide a kit including a pharmaceutical preparation containing the PD-1 agonist and a pharmaceutical preparation containing the other agent. The dose of the other agent can be appropriately selected based on the dose in clinical use. The other agent may be a combination of two or more agents at an appropriate ratio. Examples of the other agent include those already known and also those newly discovered future.

For example, in the case of applying the agent of the present invention to prophylaxis, symptom progress-suppression, and/or therapy of type I diabetes mellitus, the PD-1 agonist as an active ingredient may be used in combination with, for example, an insulin preparation (e.g., human insulin, insulin glargine, insulin lispro, insulin detemir, or insulin aspart), a sulfonylurea agent (e.g., glibenclamide, gliclazide, or glimepiride), a quick-acting insulin secretion promoter (e.g., nateglinide), a biguanide preparation (e.g., metformin), an insulin sensitizer (e.g., pioglitazone), an α-glucosidase inhibitor (e.g., acarbose or voglibose), a diabetic neuropathy therapeutic agent (e.g., epalrestat, mexiletine, or imidapril), a GLP-1 analog preparation (e.g., liraglutide, exenatide, or lixisenatide), or a DPP-4 inhibitor (e.g., sitagliptin, vildagliptin, or alogliptin).

For example, in the case of applying the agent of the present invention to prophylaxis and/or therapy of multiple sclerosis, the PD-1 agonist as an active ingredient may be used in combination with, for example, a steroid agent (e.g., cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamsinolone, triamsinolone acetate, triamsinolone acetonide, dexamethasone, dexamethasone acetate, dexamethasone sodium phosphate, dexamethasone palmitate, paramethasone acetate, or betamethasone), interferon β-1a, interferon β-1b, glatiramer acetate, mitoxantrone, azathioprine, cyclophosphamide, cyclosporin, methotrexate, cladribine, adrenocorticotropic hormone (ACTH), corticotropin, mizoribine, tacrolimus, fingolimod, or alemtuzumab.

For example, in the case of applying the agent of the present invention to prophylaxis and/or therapy of systemic lupus erythematosus, the PD-1 agonist as an active ingredient may be used in combination with a steroid agent (e.g., steroid agents mentioned above) or an immunosuppressive agent (e.g., cyclosporin, tacrolimus, or fingolimod).

For example, in the case of applying the agent of the present invention to prophylaxis and/or therapy of rheumatoid arthritis, the PD-1 agonist as an active ingredient may be used in combination with, for example, a steroid agent (e.g., steroid agents mentioned above), an anti-rheumatic agent (e.g., methotrexate, sulfasalazine, bucillamine, leflunomide, mizoribine, or tacrolimus), or an anti-cytokine agent (e.g., infliximab, adalimumab, tocilizumab, etanercept, or abatacept).

The present invention will now be described in more detail by the following examples, but the scope of the present invention is not limited thereto. Various changes and modifications can be made by those skilled in the art based on the description of the present invention, and such changes and modifications are also included in the present invention.

EXAMPLES

Example 1

Evaluation of Hypoglycemic Action of PD-1 Agonist on Spontaneous Type I Diabetes Mellitus Animal Model (NOD Mice)

Once a week, 1 to 5 µL of blood was collected from the tail vein of each NOD mouse (16-week old at the start of experiment), and the blood glucose level was measured with ACCU-CHECK active (Roche Diagnostics K.K.). Mice that had a blood glucose level of 200 mg/dL or more successive two times in measurement were determined as mice having the onset of diabetes mellitus and allocated to each group. On and after the day of the allocation, the mice were intraperitoneally or intravenously administered with 0.3, 1, or 6 µg/day of a PD-1 agonist for successive 5 days (the control group was administered with phosphate buffer). Subsequently, blood was collected once a week from each mouse, and the blood glucose level was measured as in above. The PD-1 agonist was prepared in accordance with Examples 1 to 9 in International Publication No. WO2003/011911 (US 2004/0241745, published from the U.S. counterpart application).

In all groups of doses of 0.3, 1, and 6 µg/day (total doses: 1.5, 5, and 30 µg), hypoglycemic action or normoglycemia-maintaining action was observed over at least 23 weeks from the first administration (FIGS. 2 to 4 and 6), compared to the control group (FIG. 1). In the group of a dose of 6 µg/day, the hypoglycemic action or normoglycemia-maintaining action was observed even in the 27th week from the first administration (FIG. 4), and the action in 12th to 27th weeks showed a low individual difference. The degree of action in administration of the PD-1 agonist for successive 5 days was equivalent to that in administration of 6 µg/day of the PD-1 agonist three times per week for 8 weeks (FIG. 5).

Figure 2:
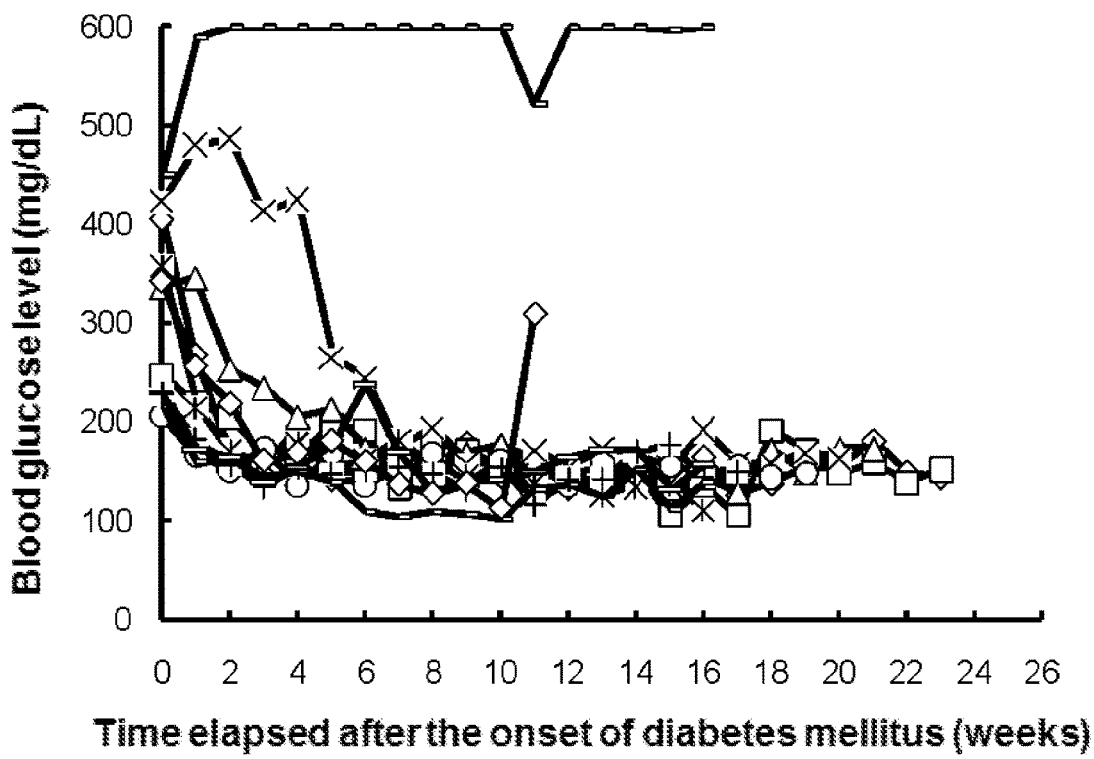
FIG. 2 shows reductions in blood glucose level in a group of spontaneous type I diabetes mellitus model mice administered with a PD-1 agonist (0.3 µg/day) for successive 5 days, wherein each line in the graph shows the result of each mouse administered with the PD-1 agonist.
Figure 3:
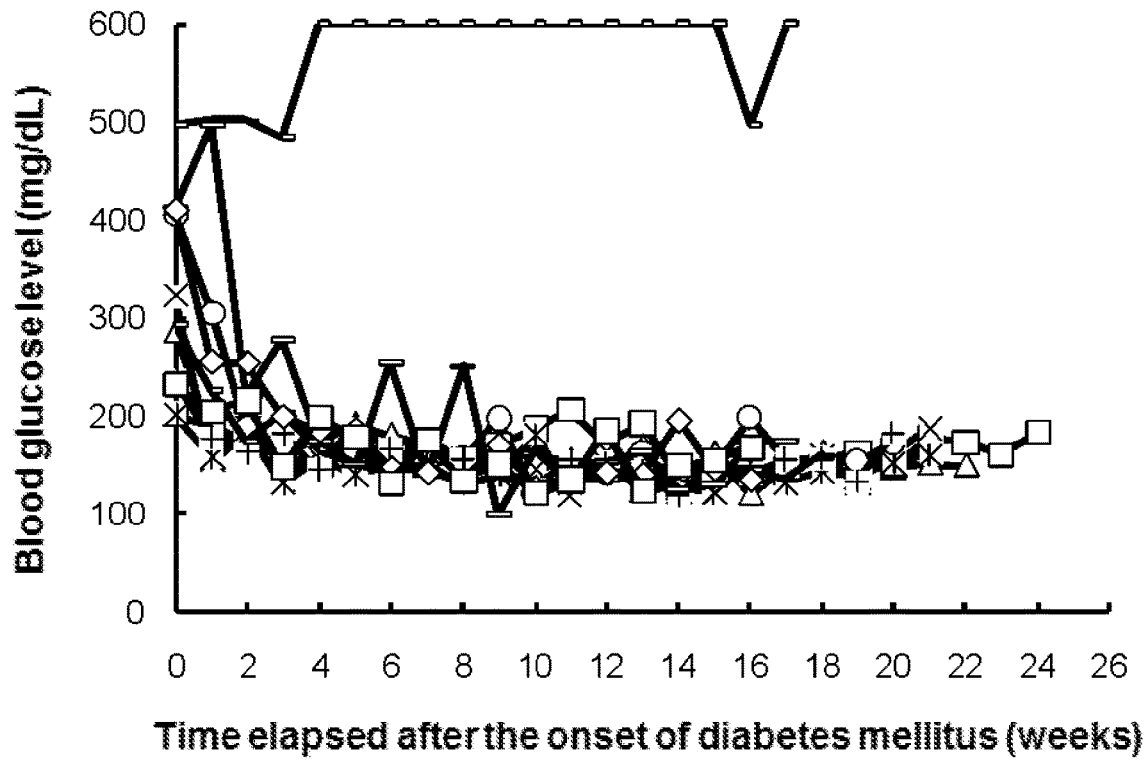
FIG. 3 shows reductions in blood glucose level in a group of spontaneous type I diabetes mellitus model mice administered with the PD-1 agonist (1 µg/day) for successive 5 days, wherein each line in the graph shows the result of each mouse administered with the PD-1 agonist.
Figure 4:
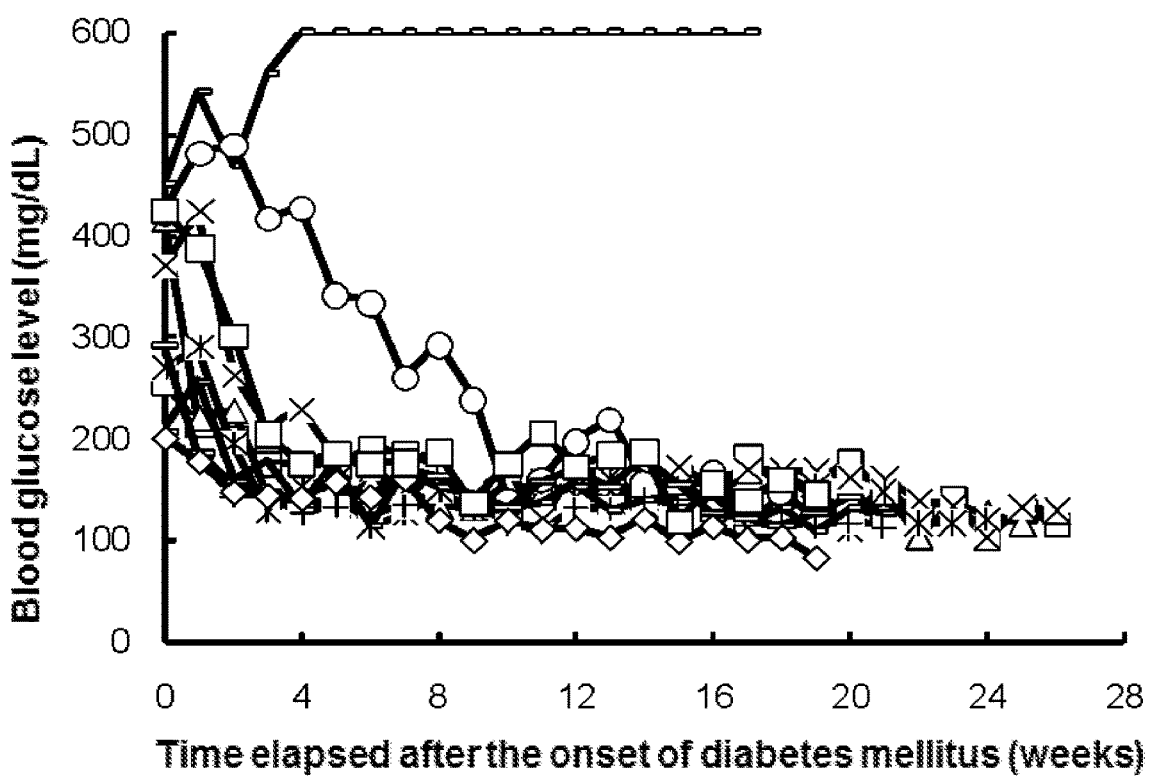
FIG. 4 shows reductions in blood glucose level in a group of spontaneous type I diabetes mellitus model mice administered with the PD-1 agonist (6 µg/day) for successive 5 days, wherein each line in the graph shows the result of each mouse administered with the PD-1 agonist.
Figure 5:
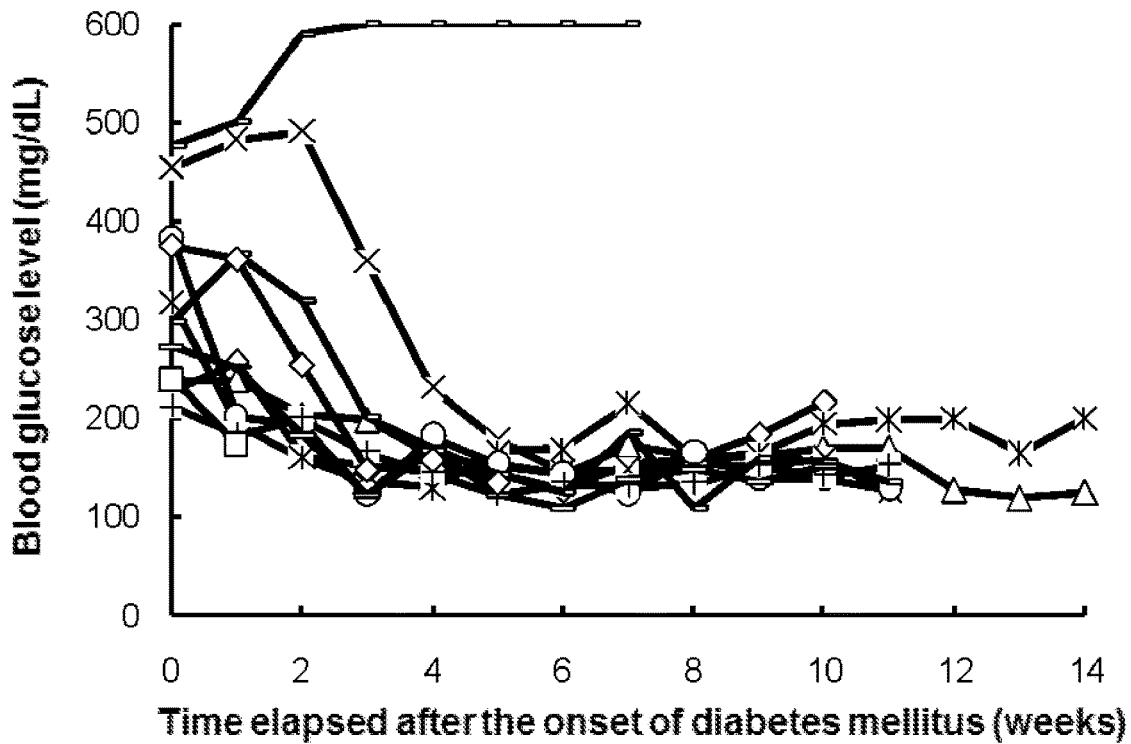
FIG. 5 shows reductions in blood glucose level in a group of spontaneous type I diabetes mellitus model mice administered with the PD-1 agonist (6 µg/day) three times per week (8 weeks), wherein each line in the graph shows the result of each mouse administered with the PD-1 agonist.
Figure 6:
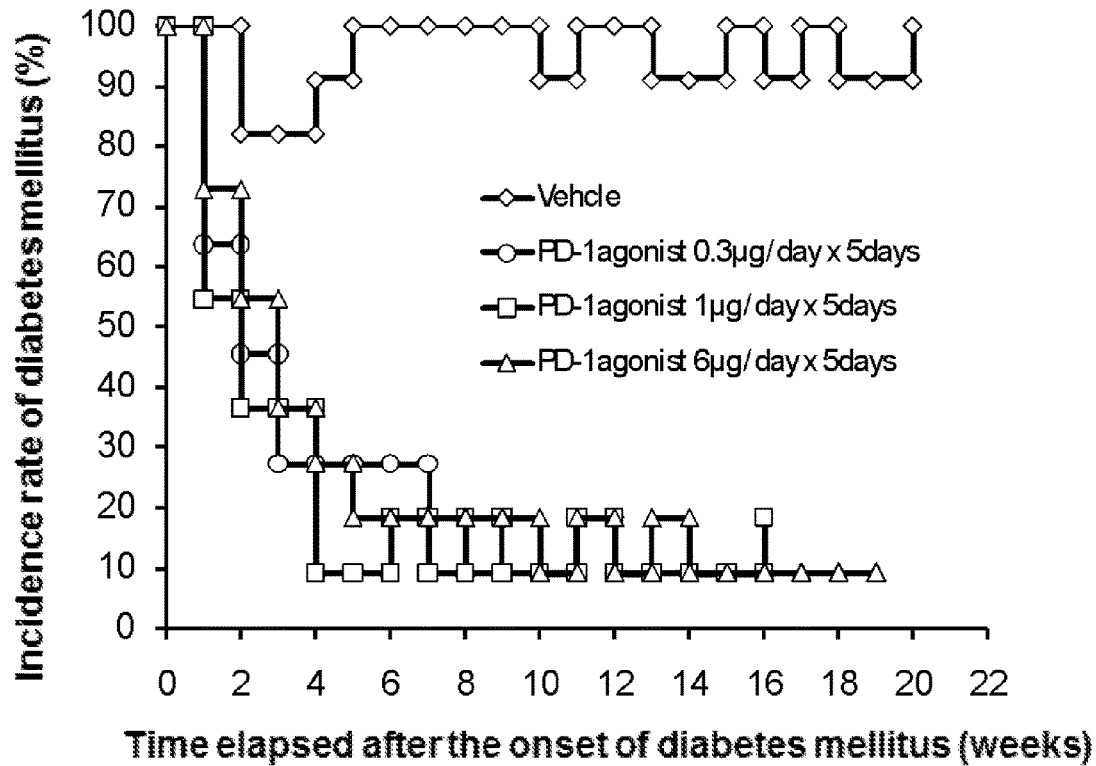
FIG. 6 shows the state of the onset of diabetes mellitus by incidence rates of spontaneous type I diabetes mellitus model mice in a control group and groups administered with the PD-1 agonist (0.3, 1, or 6 µg/day) for successive 5 days, wherein the symbols o, □, and ∆ represent the PD-1 agonist administration groups, and the symbol ◇ represents the control group.
Figure 7:
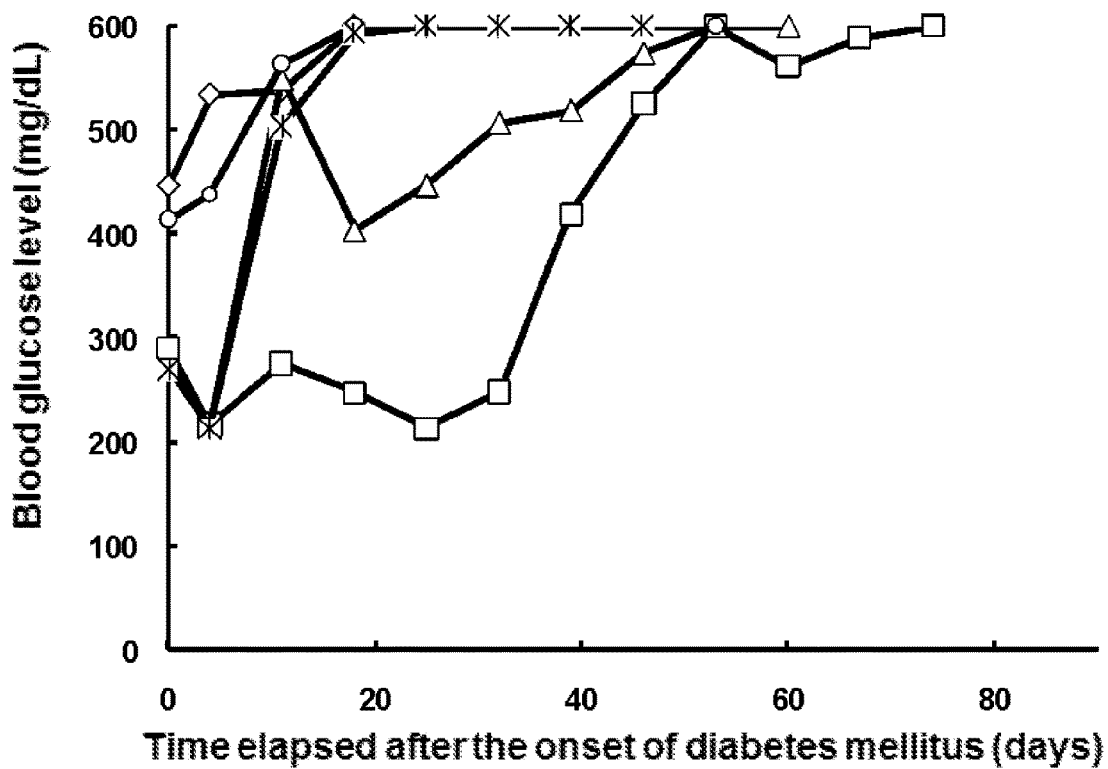
FIG. 7 shows reductions in blood glucose level in a control group of spontaneous type I diabetes mellitus model mice administered with a phosphate buffer once, wherein each line in the graph shows the result of each mouse.
Figure 8:
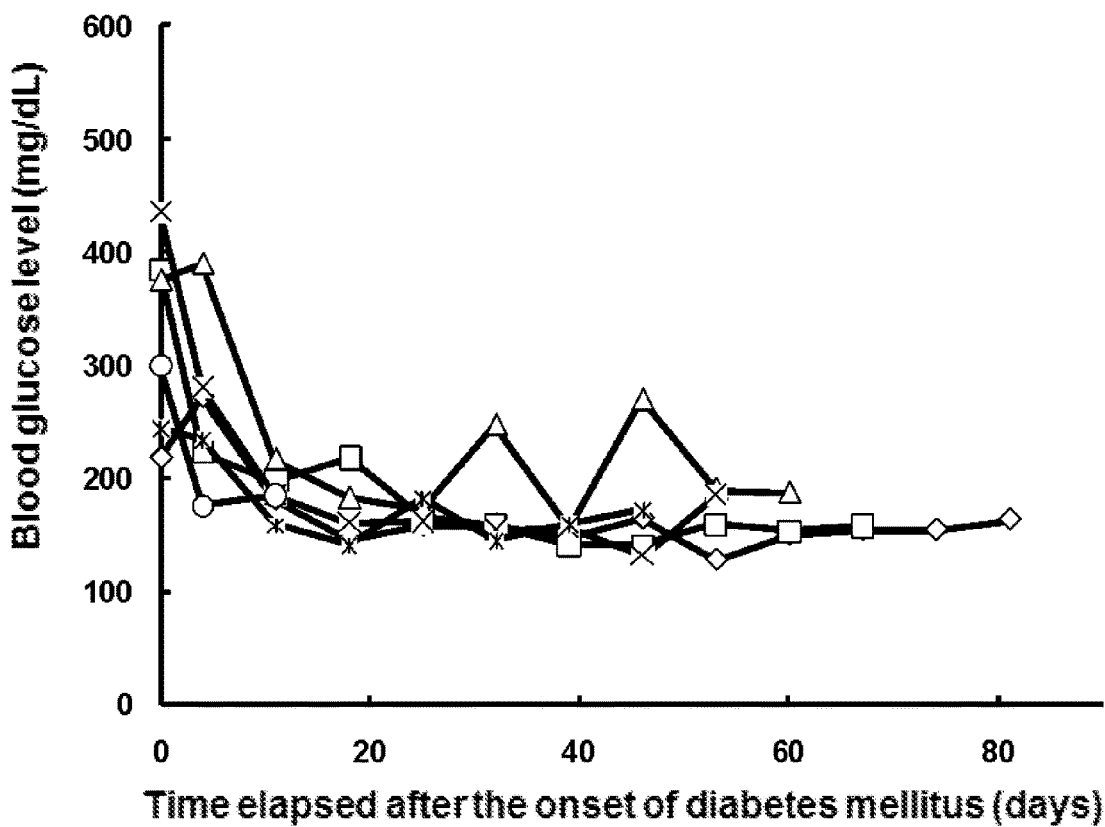
FIG. 8 shows reductions in blood glucose level in a group of spontaneous type I diabetes mellitus model mice administered with the PD-1 agonist (3 µg/day) once, wherein each line in the graph shows the result of each mouse administered with the PD-1 agonist.
Figure 9:
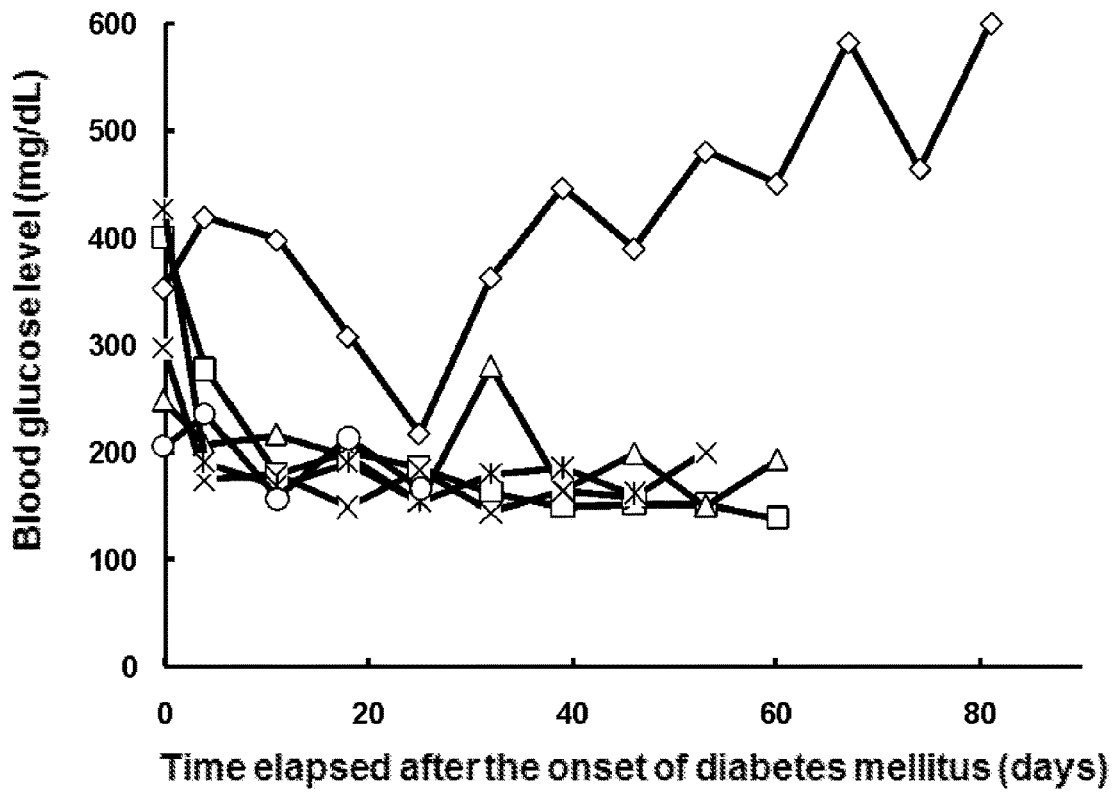
FIG. 9 shows reductions in blood glucose level in a group of spontaneous type I diabetes mellitus model mice administered with the PD-1 agonist (3 µg/day) for successive 2 days, wherein each line in the graph shows the result of each mouse administered with the PD-1 agonist.
Figure 10:
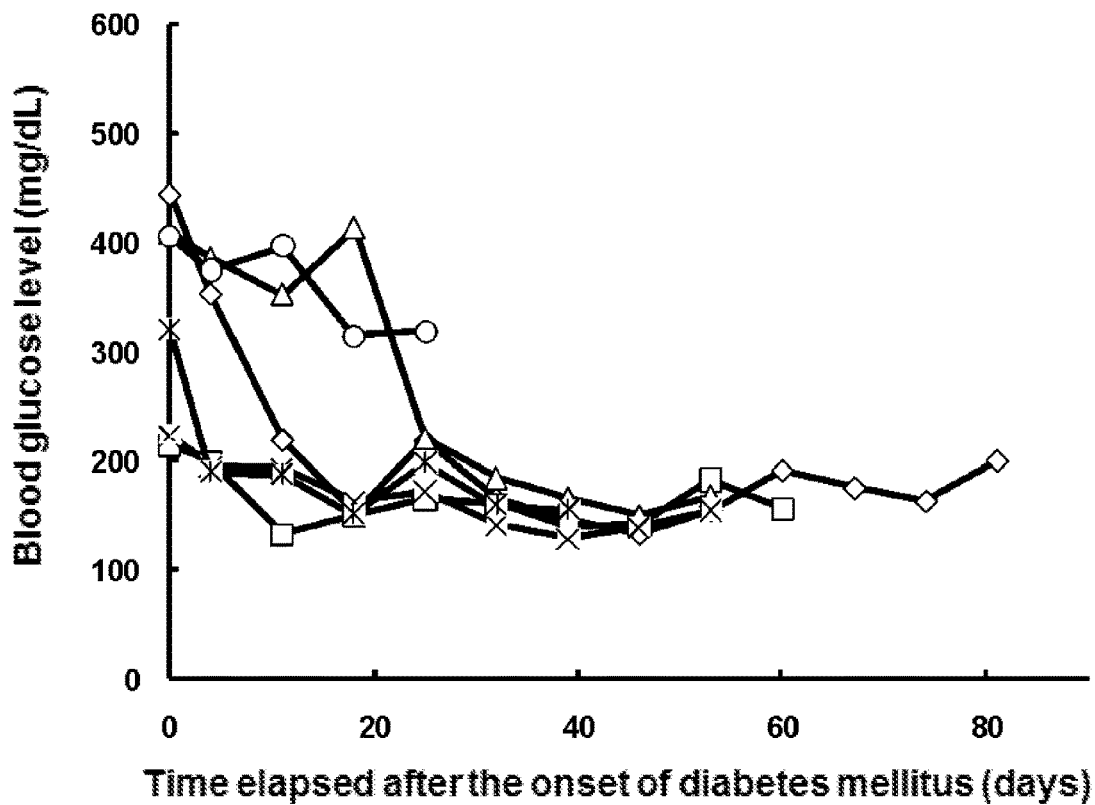
FIG. 10 shows reductions in blood glucose level in a group of spontaneous type I diabetes mellitus model mice administered with the PD-1 agonist (3 µg/day) for successive 3 days, wherein each line in the graph shows the result of each mouse administered with the PD-1 agonist.
Figure 11:
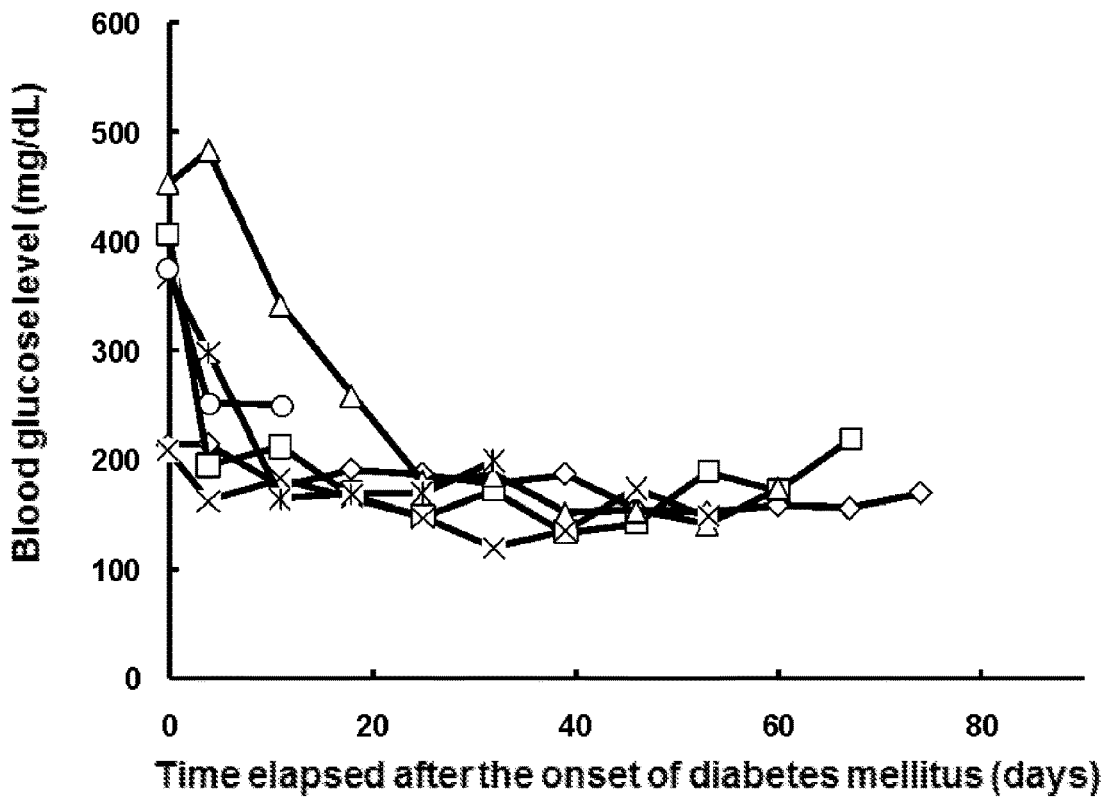
FIG. 11 shows reductions in blood glucose level in a group of spontaneous type I diabetes mellitus model mice administered with the PD-1 agonist (3 µg/day) for successive 4 days, wherein each line in the graph shows the result of each mouse administered with the PD-1 agonist.
Figure 12:
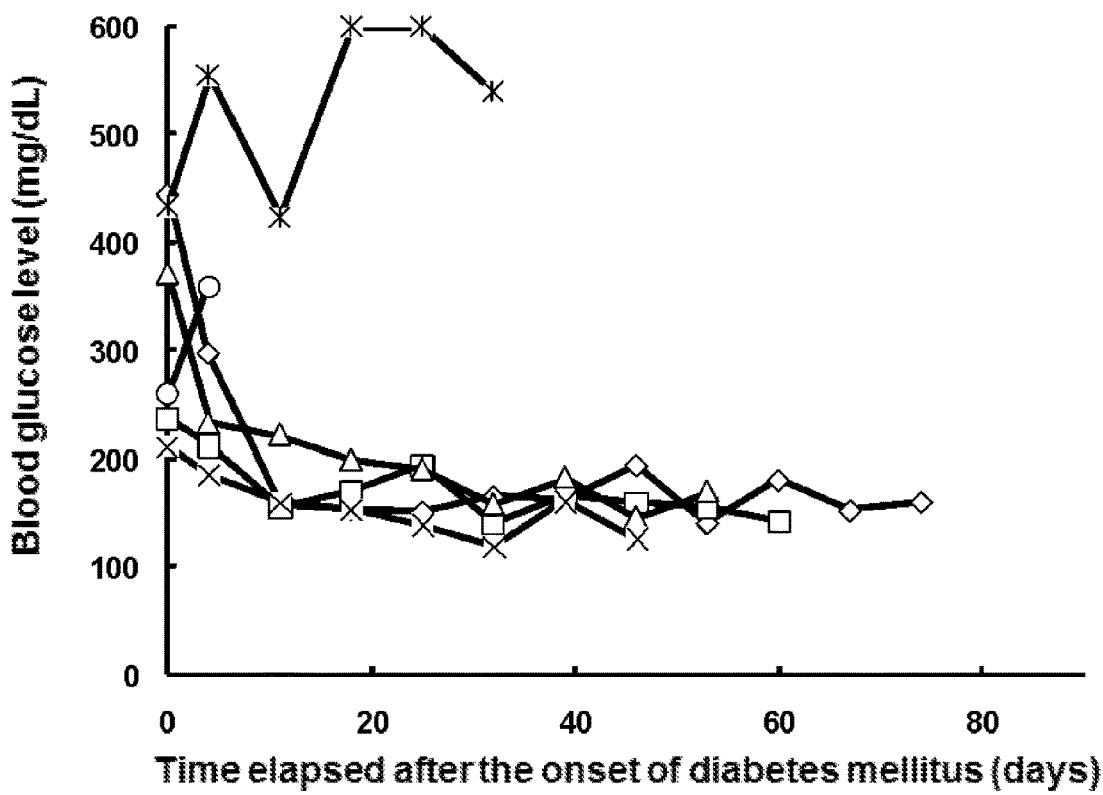
FIG. 12 shows reductions in blood glucose level in a group of spontaneous type I diabetes mellitus model mice administered with the PD-1 agonist (3 µg/day) for successive 5 days, wherein each line in the graph shows the result of each mouse administered with the PD-1 agonist.

In also groups of administration of 3 µg/day of the PD-1 agonist for once or successive 2, 3, 4, or 5 days, the hypoglycemic action or normoglycemia-maintaining action equivalent to those shown in FIGS. 2 to 4 was observed (FIGS. 8 to 12), compared to the control group (FIG. 7). In observation for 52 weeks from the administration at the longest, the hypoglycemic action or normoglycemia-maintaining action was observed in the group of administration of a dose of 3 µg/day once.

Example 2

Evaluation (1) of Therapeutic Effect of PD-1 Agonist on Multiple Sclerosis Animal Model (Experimental Autoimmune Encephalomyelitis: EAE)

A phosphate buffer containing 4 mg/mL of myelin oligodendrocyte glycoprotein (MOG) and the same quantity of complete adjuvant H37Ra (Nippon Becton Dickinson Company, Ltd.) were mixed to prepare an emulsion, which was used as an initiating agent. The prepared initiating agent (100 µL) was subcutaneously injected at the tail base of each mouse. Each mouse was administered with 200 µL of a phosphate buffer containing 1 µg/mL of P pertussis toxin (SIGMA-ALDRICH) in the tail vein on the day and the next day of the first immunization with the initiating agent.

Figure 13:
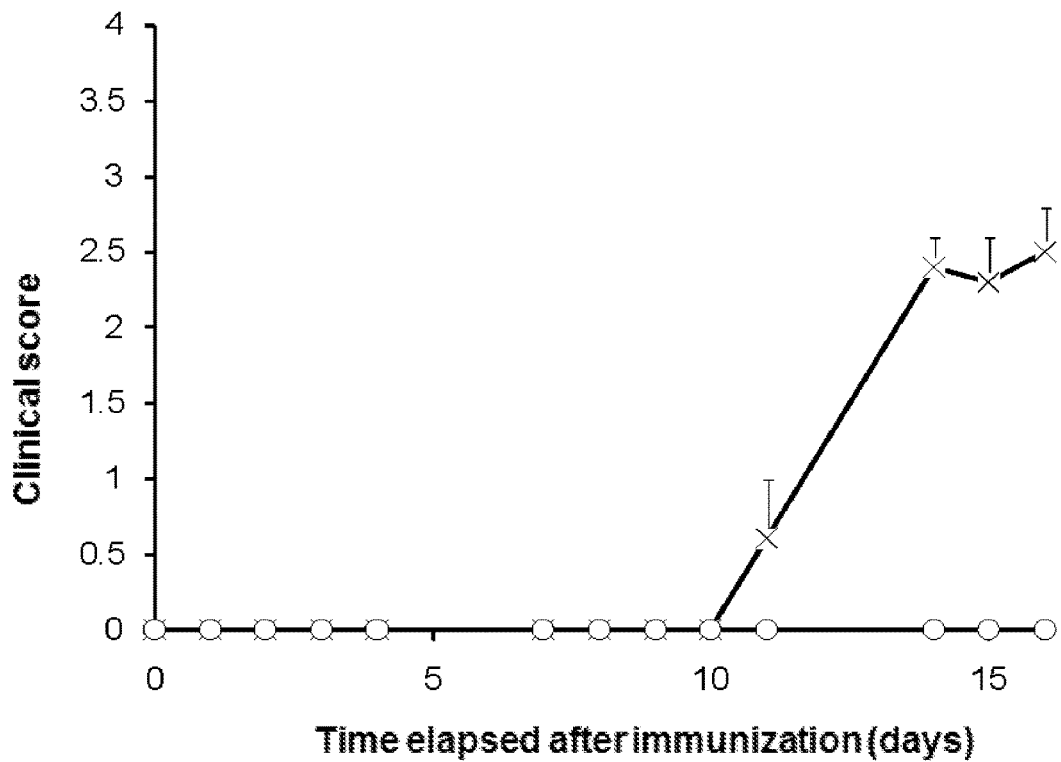
FIG. 13 shows an effect of suppressing the onset of multiple sclerosis by administration of the PD-1 agonist (3 µg/day) to multiple sclerosis (experimental autoimmune encephalomyelitis: EAE) model mice for successive 5 days from the day of immunization, wherein the symbol o represents the PD-1 agonist administration group, and the symbol x represents a control group (phosphate buffer administration group)
Figure 14:
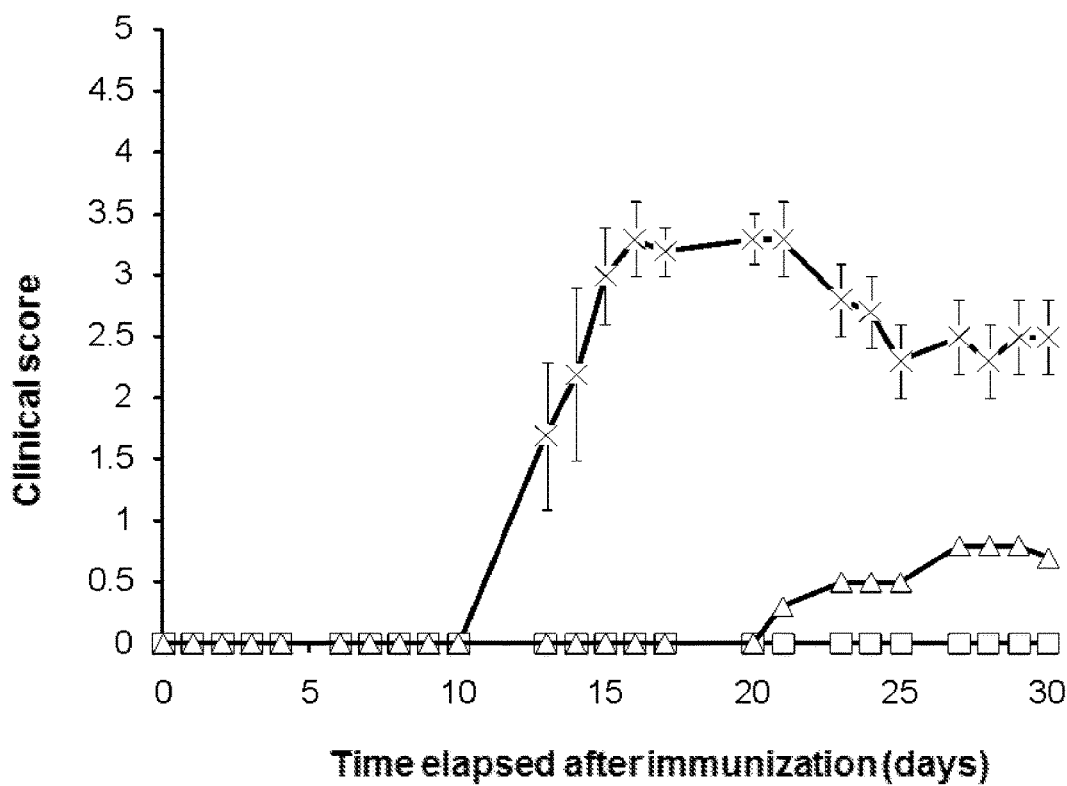
FIG. 14 shows an effect of suppressing the onset of multiple sclerosis by administration of the PD-1 agonist for successive 5 days from the day of immunization or for successive 5 days from the 6th day after the immunization of multiple sclerosis model mice, wherein the symbol □ represents the group administered with 6 µg/day of the PD-1 agonist for successive 5 days from the day of immunization, the symbol ∆ represents the group administered with 6 µg/day of the PD-1 agonist for successive 5 days from the 6th day after the immunization, and the symbol x represents a control group (phosphate buffer administration group)
Figure 15:
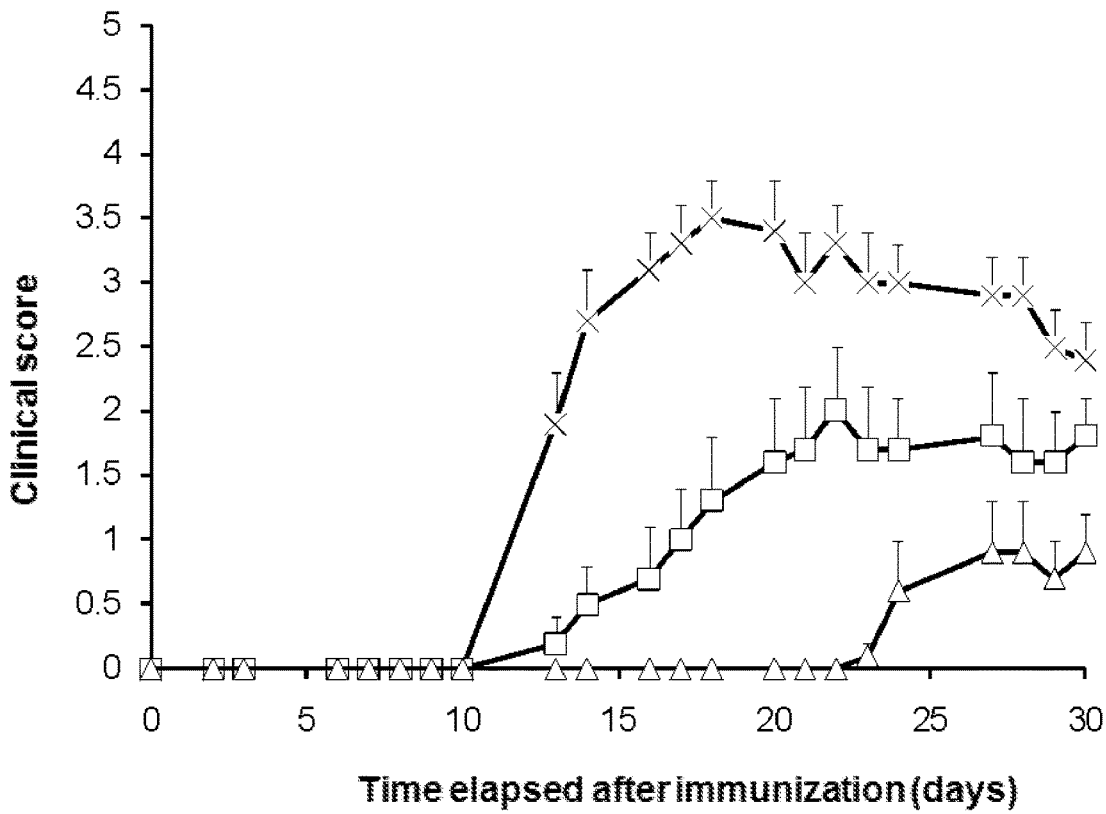
FIG. 15 shows an effect of suppressing the onset of multiple sclerosis by administration of the PD-1 agonist to multiple sclerosis model mice for successive 5 days from the 6th day after the immunization, wherein the symbol □ represents a group administered with 1 µg/kg/day of the PD-1 agonist for successive 5 days, the symbol ∆ represents a group administered with 3 µg/kg/day of the PD-1 agonist for successive 5 days, and the symbol x represents a control group (phosphate buffer administration group)
Figure 16:
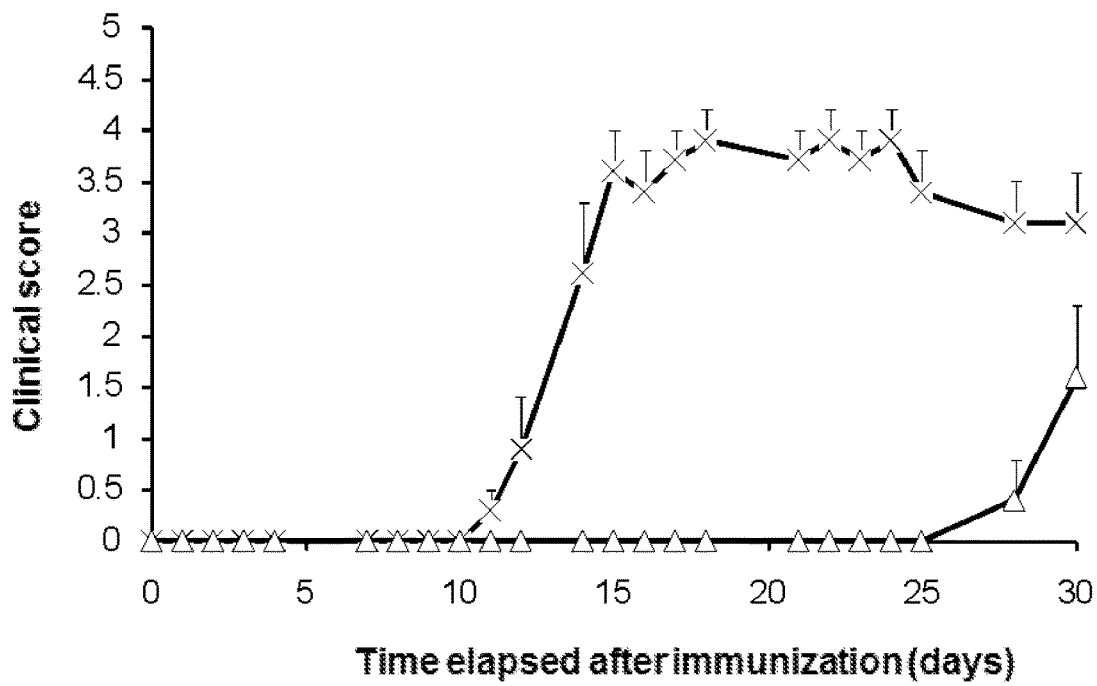
FIG. 16 shows an effect of suppressing the onset of multiple sclerosis by administration of the PD-1 agonist for successive 5 days from the 7th day after the immunization of multiple sclerosis model mice, wherein the symbol ∆ represents a group administered with 6 µg/day of the PD-1 agonist from the 7th day after the immunization, and the symbol x represents a control group (phosphate buffer administration group)
Figure 17:
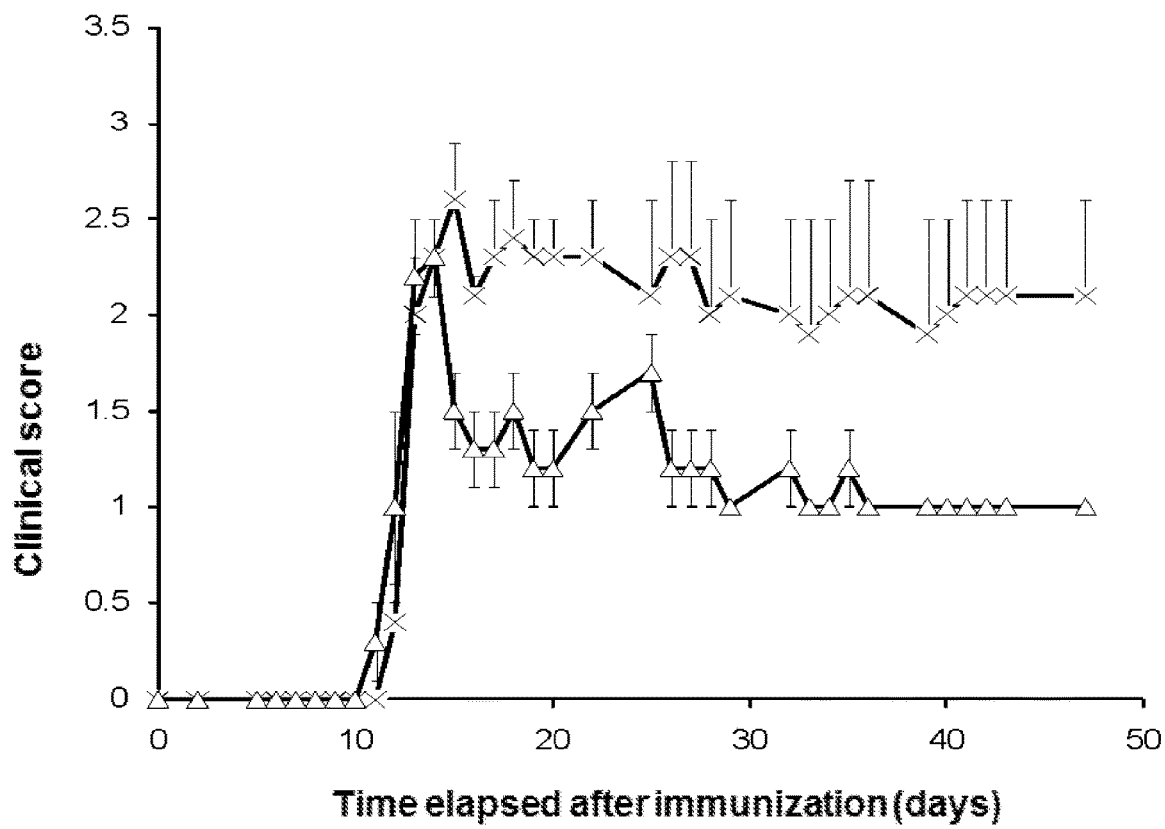
FIG. 17 shows a therapeutic effect on multiple sclerosis by administration of the PD-1 agonist to multiple sclerosis model mice for successive 5 days from the 13th day after the immunization, wherein the symbol ∆ represents a group administered with 0.3 µg/kg/day of the PD-1 agonist for successive 5 days from the 13th day after the immunization, and the symbol x represents a control group (phosphate buffer administration group)

The mice were administered with 3 µg/day or 6 µg/day of the PD-1 agonist for successive 5 days from the day of the first immunization with the initiating agent (FIGS. 13 and 14). In other groups, the mice were administered with 1 µg/day, 3 µg/day, or 6 µg/day of the PD-1 agonist for successive 5 days from the 6th or 7th day after the first immunization (0th day) with the initiating agent (FIGS. 14 to 16). In another group, the mice were administered with 0.3 µg/day of the PD-1 agonist for successive 5 days from the 13th day, on which all mice developed EAE, after the immunization with the initiating agent (FIG. 17).

The neurological symptoms after the immunization were evaluated in accordance with the method of Ohnuki, et al. (Microscopy research and technique, 2001, Vol. 252, pp. 731-739). That is, the degrees of paralysis were scored (normal: 0, tail relaxation: 1, hind limb partial paralysis: 2, hind limb paralysis: 3, forelimb paralysis: 4, and dying or death: 5). If a plurality of symptoms were observed, the higher score was employed as the neurological symptom on the evaluation day. The neurological symptom of died mice was scored to 5 until completion of the observation. The dying mice were euthanized with a carbon dioxide gas.

In the groups in which the administration of the PD-1 agonist was started on the day of the first immunization with the initiating agent, the onset of EAE was completely suppressed in all cases of different doses. In the group of administration of 6 µg/day, the suppression effect was maintained until 30 days from the immunization. When the administration of the PD-1 agonist was started on the 6th or 7th day from the first immunization, the onset of EAE was suppressed for 20 to 22 days in the PD-1 agonist administration groups, whereas the control group (phosphate buffer administration group) developed EAE about the 10th day and deteriorated the EAE symptoms. Similarly, even in the group of starting the administration of the PD-1 agonist on the 13th day from the first immunization, deterioration of EAE symptoms was significantly suppressed. The therapeutic effect in the case of starting the administration of the PD-1 agonist on the 13th day from the first immunization was equivalent to that in the case of administration of the same dose per day of the PD-1 agonist 3 times per week until the 43rd day.

It was confirmed from the above that the PD-1 agonist has a prophylactic and therapeutic effects on the onset of EAE even with a small number of times of administration.

Example 3

Evaluation (2) of Therapeutic Effect of PD-1 Agonist on Multiple Sclerosis Animal Model The effects of a PD-1 agonist on multiple sclerosis model mice produced as in Example 2 were evaluated by the following method. The neurological symptoms were also evaluated as in Example 2.

Figure 18:
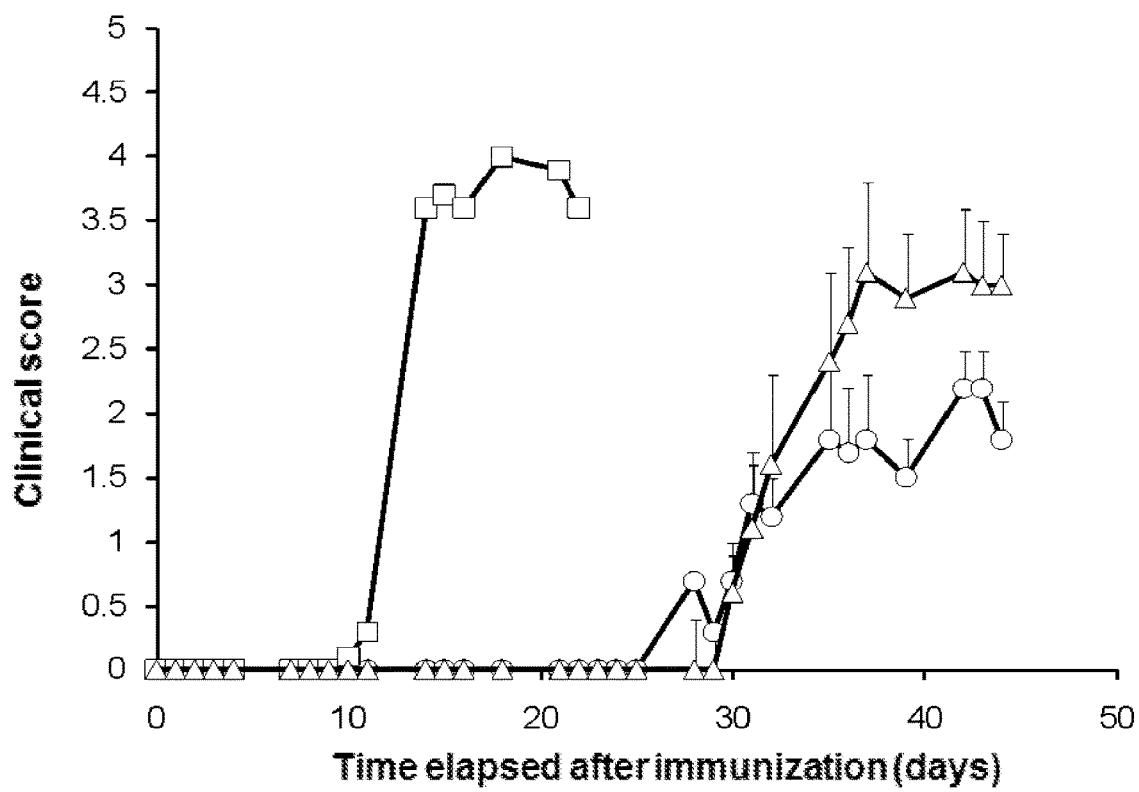
FIG. 18 shows an effect of suppressing the onset of multiple sclerosis by the PD-1 agonist for multiple sclerosis model mice, wherein the symbol o represents a group immunized with an initiating agent twice, on the 0th and 22nd days, and administered with 0.22 mg/kg/day of the PD-1 agonist for successive 5 days from the 7th day after the first immunization (0th day) with the initiating agent, the symbol □ represents a group immunized with the initiating agent on the 0th day and administered with a phosphate buffer for successive 5 days from the 7th day, and the symbol Δ represents a group immunized with the initiating agent on the 22nd day, without performing the immunization with the initiating agent on the 0th day, and administered with a phosphate buffer for successive 5 days from the 7th day.

A group immunized with an initiating agent twice, on the 0th and 22nd days, and administered with 0.22 mg/kg/day of the PD-1 agonist for successive 5 days from the 7th day after the first immunization (0th day) with the initiating agent was specified as group A (in FIG. 18, the group represented by symbol o). A group administered with the PD-1 agonist as in group A and then immunized with the initiating agent on the 22nd day, without performing the immunization with the initiating agent on the 0th day, was specified as group B (in FIG. 19, the group represented by symbol o). A group immunized with the initiating agent on the 0th day and administered with a phosphate buffer for successive 5 days from the 7th day was specified as group C (in FIG. 18, the group represented by symbol □). A group immunized with the initiating agent on the 22nd day, without performing the immunization with the initiating agent on the 0th day, and administered with a phosphate buffer for successive 5 days from the 7th day was specified as group D (in FIG. 18, the group represented by symbol Δ, and in FIG. 19, the group represented by symbol □). The PD-1 agonist was prepared in accordance with the document referred in Example 1 and used.

Figure 19:
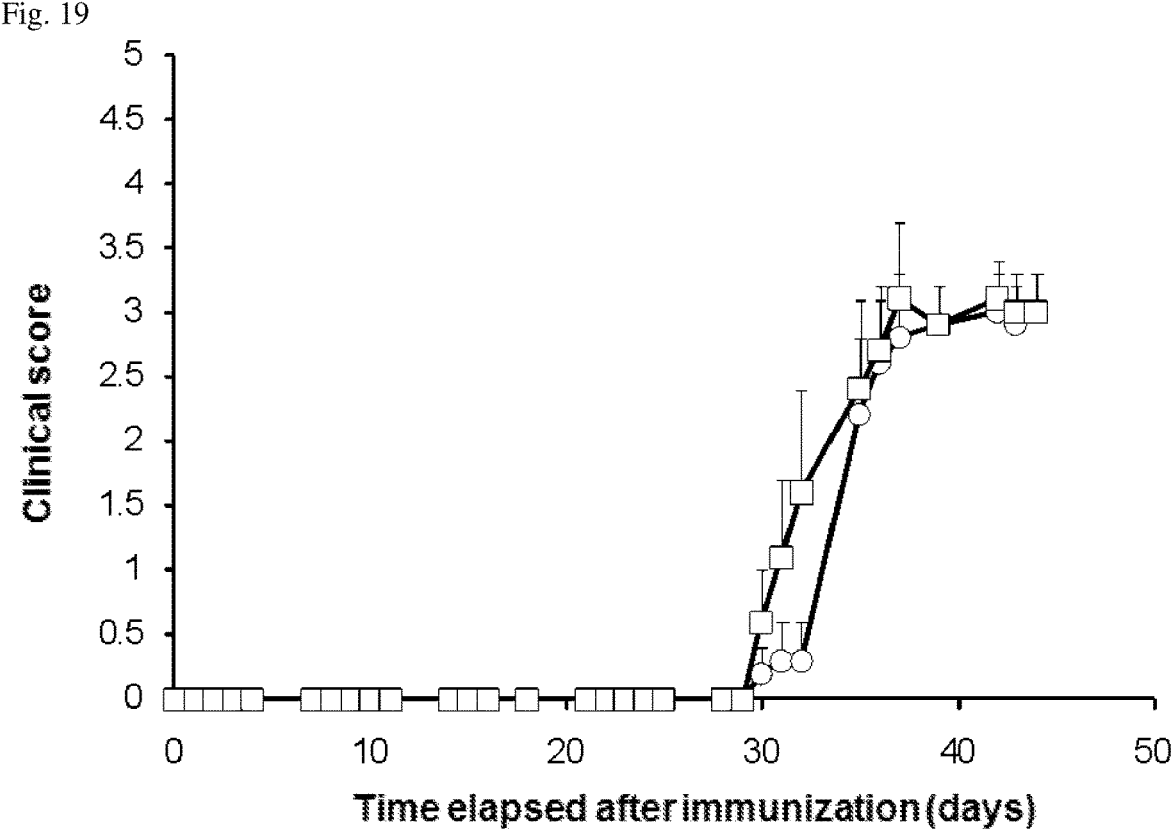
FIG. 19 shows an effect of suppressing the onset of multiple sclerosis by the PD-1 agonist for multiple sclerosis model mice, wherein, as in the experiment shown in FIG. 18, the symbol o represents a group immunized with the initiating agent on the 22nd day, without performing the immunization with the initiating agent on the 0th day, and administered with 0.22 mg/kg/day of the PD-1 agonist for successive 5 days from the 7th day, and the symbol □ represents a group immunized with the initiating agent on the 22nd day, without performing the immunization with the initiating agent on the 0th day, and administered with a phosphate buffer for successive 5 days from the 7th day.

As shown in FIG. 18, in group A administered with the PD-1 agonist for successive 5 days, the onset of EAE symptoms was completely suppressed even around the 11th day, compared to group C developing the EAE symptoms on and after around the 11th day after the immunization on the 0th day. In addition, in group A, the neurological symptoms to the second immunization was significantly improved, compared to group D developing the neurological symptoms on and after around 30th day due to the immunization on the 22nd day. The results demonstrate that the PD-1 agonist suppressing the onset of EAE against the immunization on the 0th day also shows an immunosuppressive effect against the similar immunization performed 10 or more days later, whereas as shown in FIG. 19, in group B administered with the PD-1 agonist before initiation of immunity, the neurological symptoms were not improved against the immunization performed 10 or more days later, similar to the results in group D.

The results above suggest that the PD-1 agonist shows an antigen-specific suppression effect on the immune response caused by an antigen and sustains the effect, but does not show any antigen-non-specific suppression effect.

Example 4

Evaluation of Therapeutic Effect of PD-1 Agonist on Colitis Animal Model

Cell sorting with autoMACS (Miltenyi Biotec) was performed using CD4+T Cell Isolation kit II (mouse) (Miltenyi Biotec), CD25 MicroBeads kit (Miltenyi Biotec), PE-labeled anti-mouse CD45RB antibody (BD Biosciences), and Anti-PE MicroBeads (Miltenyi Biotec), and CD4+CD25-CD45RB$^{high}$ T-cells were purified from BALB/c mouse spleen cells. The CD4+CD25-CD45RB$^{high}$ T-cells were adoptively transferred into SCID mice ($4 \times 10^5$ cells/mouse, intraperitoneal administration) to cause colitis. The PD-1 agonist was intraperitoneally administered to the mice developed colitis in 4 to 5 weeks after the adoptive cell transfer.

Colitis was evaluated in accordance with the method of Cooper, et al. (Laboratory Investigation, 1993, vol. 69, No. 2, pp. 238-249). That is, the total score of weight score (rate of weight loss of 0% to 1%: 0, 1% to 5%: 1, 5% to 10%: 2, 10% to 20%: 3, >20%: 4), diarrhea score (normal: 0, unformed stool: 2, diarrhea: 4), and blood feces score (normal: 0, occult blood: 2, visible bleeding: 4) was used as colitis symptom score.

Figure 20:
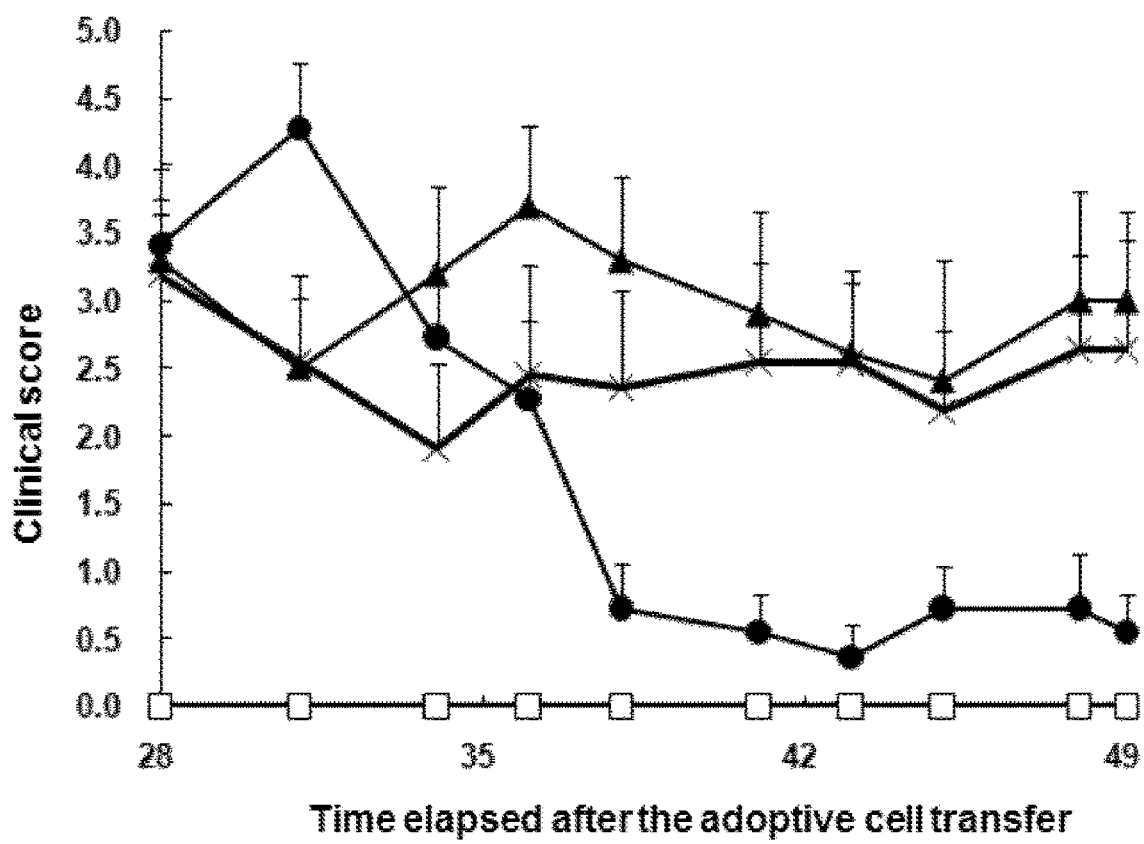
FIG. 20 shows an effect of suppressing the onset of colitis by the PD-1 agonist for colitis model mice, wherein the symbol ● represents a group administered with 6 μg/mouse of the PD-1 agonist 2 or 3 times per week (2 weeks), the symbol x represents a group administered with 10 mg/kg/day of prednisolone once a day, the symbol ▲ represents a control group, and the symbol □ represents a normal control group.
Figure 21:
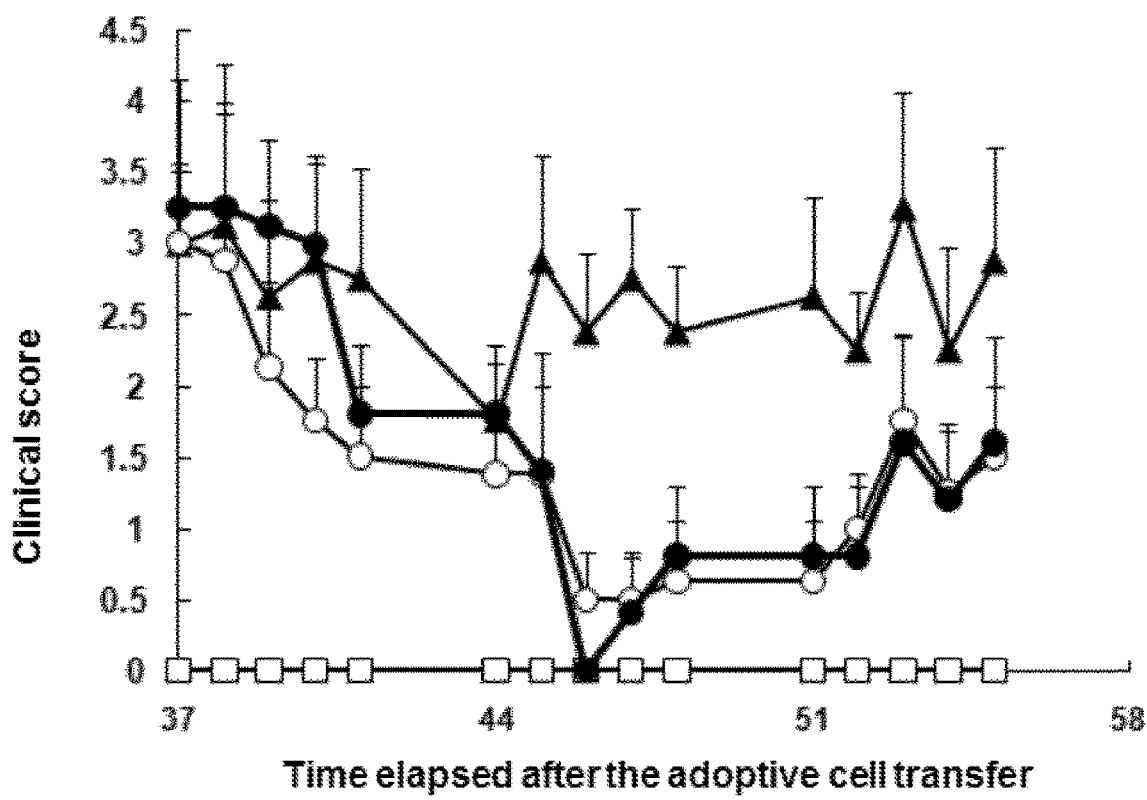
FIG. 21 shows an effect of suppressing the onset of colitis by the PD-1 agonist for colitis model mice, wherein the symbol o represents a group administered with 1 μg/mouse of the PD-1 agonist for successive 5 days, the symbol ● represents a group administered with 3 μg/mouse of the PD-1 agonist for successive 5 days, the symbol ▲ represents a control group, and the symbol □ represents a normal control group.

As shown in FIG. 21, the group administered with 3 μg/mouse of the PD-1 agonist for successive 5 days showed a therapeutic effect equivalent to that in the group (FIG. 20) administered with 6 μg/mouse of the PD-1 agonist 2 or 3 times per week (2 weeks). The effect was also sustained in the group administered with 1 μg/mouse of the PD-1 agonist for successive 5 days.

INDUSTRIAL APPLICABILITY

The prophylactic or therapeutic agent for an autoimmune disease of the present invention can sustain the therapeutic effect, while lowering the risk of infections and therefore can advantageously reduce the burden of management of the administration by a patient or medical personnel.

The invention claimed is:

1. A symptom progress-suppressive and/or therapeutic method for treating an autoimmune disease, comprising administering an agent comprising a PD-1 agonist as an active ingredient to a subject,
  wherein the method comprises an administration period and a break period following the administration period,
  wherein (a) the administration period is of one month or less and comprises 1 to 10 times of the administration of the agent, (b) a total dose of the PD-1 agonist of the administration period is 20 μg/kg or more, and (c) the break period, during which the agent is not administered to the subject, ends at least 3 months after a last administration of the administration period, and
  wherein the PD-1 agonist is an anti-PD-1 agonist antibody or an anti-PD-1-CD3 bispecific antibody.

2. The method according to claim 1, wherein the autoimmune disease comprises Behcet disease, systemic lupus erythematosus, multiple sclerosis, scleroderma, polymyositis, dermatomyositis, periarteritis nodosa, aortitis syndrome, malignant rheumatoid arthritis, rheumatoid arthritis, Wegner's granulomatosis, mixed connective tissue disease, Sjogren syndrome, adult-onset Still's disease, allergic granulomatous angiitis, hypersensitivity angiitis, Cogan's syndrome, RS3PE, temporal arteritis, polymyalgia rheumatica, fibromyalgia syndrome, antiphospholipid antibody syndrome, eosinophilic fasciitis, IgG4-related diseases, Guillain-Barre syndrome, myasthenia gravis, chronic atrophic gastritis, autoimmune hepatitis, primary biliary cirrhosis, aortitis syndrome, Goodpasture's syndrome, rapidly progressive glomerulonephritis, megaloblastic anemia, autoimmune hemolytic anemia, autoimmune neutropenia, idiopathic thrombocytopenic purpura, Graves' disease, Hashimoto's thyroiditis, autoimmune adrenal insufficiency, primary hypothyroidism, idiopathic Addison's disease, type I diabetes mellitus, chronic discoid lupus erythematosus, localized scleroderma, psoriasis, psoriatic arthritis, pemphigus, pemphigoid, herpes gestationis, linear IgA bullous skin disease, epidermolysis bullosa acquisita, alopecia areata, vitiligo, Harada disease, autoimmune optic neuropathy, idiopathic azoospermia, recurrent fetal loss, and inflammatory bowel diseases.

3. The method according to claim 2, wherein the bowel disease is ulcerative colitis or Crohn's disease.

4. The method according to claim 1, wherein the break period ends at least 6 months after the last administration.

5. The method according to claim 1, wherein the break period ends at least 9 months after the last administration.

6. The method according to claim 1, wherein the break period ends at least 12 months after the last administration.

7. The method according to claim 1, wherein the break period ends at least 24 months after the last administration.

8. The method according to claim 1, wherein the administration period is of 19 days.

9. The method according to claim 1, wherein the administration period is of 15 days.

10. The method according to claim 1, wherein the administration period is of 8 days and comprises 1 to 9 times of the administration of the agent.

11. The method according to claim 1, wherein the administration period is of 5 days and comprises 1 to 6 times of the administration of the agent.

12. The method according to claim 1, wherein the administration period is of 1 day and comprises once of the administration of the agent.

13. The method according to claim 1, wherein the total dose of the PD-1 agonist is 20 to 1,250 µg/kg.

14. The method according to claim 1, wherein the total dose of the PD-1 agonist is 20 to 960 µg/kg.

15. The method according to claim 1, wherein the anti-PD-1-CD3 bispecific antibody is an anti-PD-1-CD3 bispecific sc(Fv)$_2$.

16. The method according to claim 1, wherein the CD3 binding part of the anti-PD-1-CD3 bispecific antibody is derived from OKT3.

17. A method for sustaining a symptom progress-suppressive and/or therapeutic effect in an autoimmune disease for at least 3 months after a last administration of a PD-1 agonist, comprising administering the PD-1 agonist to a patient having the autoimmune disease,
wherein the method comprises an administration period and a break period following the administration period,
wherein the administration period is of one month or less and comprises 1 to 10 times of the administration of the PD-1 agonist at a total dose of 20 µg/kg or more, and the break period, during which the PD-1 agonist is not administered to the subject, ends at least 3 months after the last administration of the administration period, and wherein the PD-1 agonist is an anti-PD-1 agonist antibody or an anti-PD-1-CD3 bispecific antibody.

18. A symptom progress-suppressive and/or therapeutic method for an autoimmune disease, comprising administering an agent comprising a PD-1 agonist as an active ingredient to a subject,
wherein the method comprises an administration period and a break period following the administration period,
wherein (a) the administration period is of one month or less and comprises 1 to 10 times of the administration of the agent,
(b) a total dose of the PD-1 agonist in of the administration period is 20 µg/kg or more, and
(c) the break period, during which the agent is not administered to the subject, ends at least 3 months after a last administration of the administration period, and wherein the PD-1 agonist is an anti-PD-1 agonist antibody or an anti-PD-1-CD3 bispecific antibody.

19. A symptom progress-suppressive and/or therapeutic method for treating an autoimmune disease, comprising administering an agent comprising a PD-1 agonist as an active ingredient to a subject,
wherein the method comprises an administration period and a break period following the administration period,
wherein (a) the administration period is of one month or less and comprises 2 to 10 times of the administration of the agent,
(b) a total dose of the PD-1 agonist of the administration period is 20 µg/kg or more, and
(c) the break period, during which the agent is not administered to the subject, ends at least 3 months after a last administration of the administration period.

20. A method for sustaining a symptom progress-suppressive and/or therapeutic effect in an autoimmune disease for at least 3 months after a last administration of a PD-1 agonist, comprising administering the PD-1 agonist to a patient having the autoimmune disease,
wherein the method comprises an administration period and a break period following the administration period,
wherein the administration period is of one month or less and comprises 2 to 10 times of the administration of the PD-1 agonist at a total dose of 20 µg/kg or more, and the break period, during which the PD-1 agonist is not administered to the subject, ends at least 3 months after the last administration of the administration period.

21. A symptom progress-suppressive and/or therapeutic method for an autoimmune disease, comprising administering an agent comprising a PD-1 agonist as an active ingredient to a subject,
wherein the method comprises an administration period and a break period following the administration period,
wherein (a) the administration period is of one month or less and comprises 2 to 10 times of the administration of the agent,
(b) a total dose of the PD-1 agonist in of the administration period is 20 µg/kg or more, and
(c) the break period, during which the agent is not administered to the subject, ends at least 3 months after a last administration of the administration period.

* * * * *

UNITED STATES PATENT AND TRADEMARK OFFICE
CERTIFICATE OF CORRECTION

PATENT NO. : 10,647,770 B2  
APPLICATION NO. : 15/619269  
DATED : May 12, 2020  
INVENTOR(S) : Shiro Shibayama and Masamichi Imai Page 1 of 1

It is certified that error appears in the above-identified patent and that said Letters Patent is hereby corrected as shown below:

In the Claims

In Claim 18, Column 38, Line 1, after "agonist", delete "in"; and

In Claim 21, Column 38, Line 45, after "agonist", delete "in".

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*